US009687428B2

(12) United States Patent
Singh et al.

(10) Patent No.: US 9,687,428 B2
(45) Date of Patent: *Jun. 27, 2017

(54) HYDROGEL COMPOSITIONS FOR TOOTH WHITENING

(71) Applicants: A.V.Topchiev Institute of Petrochemical Synthesis, Russian Academy of Sciences, Moscow (RU); Corium International, Inc., Menlo Park, CA (US)

(72) Inventors: Parminder Singh, Union City, CA (US); Gary W. Cleary, Los Altos Hills, CA (US); Sri Mudumba, Union City, CA (US); Mikhail M. Feldstein, Moscow (RU); Danir F. Bayramov, Irvine, CA (US)

(73) Assignees: A. V. TOPCHIEV INSTITUTE OF PETROCHEMICAL SYNTHESIS, RUSSIAN ACADEMY OF SCIENCES, Moscow (RU); CORIUM INTERNATIONAL, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/360,938

(22) Filed: Nov. 23, 2016

(65) Prior Publication Data

US 2017/0071833 A1 Mar. 16, 2017

Related U.S. Application Data

(63) Continuation of application No. 14/494,304, filed on Sep. 23, 2014, now Pat. No. 9,532,935, which is a continuation of application No. 10/359,548, filed on Feb. 5, 2003, now Pat. No. 8,840,918, which is a continuation-in-part of application No. 10/137,664, filed on May 1, 2002, now Pat. No. 8,728,445.

(60) Provisional application No. 60/288,008, filed on May 1, 2001.

(51) Int. Cl.
| | |
|---|---|
| A61K 8/22 | (2006.01) |
| A61Q 11/02 | (2006.01) |
| A61K 6/00 | (2006.01) |
| A61K 8/81 | (2006.01) |
| A61K 8/04 | (2006.01) |
| A61C 19/06 | (2006.01) |
| A61K 8/02 | (2006.01) |
| A61K 8/73 | (2006.01) |
| A61K 8/86 | (2006.01) |
| A61L 15/60 | (2006.01) |
| A61Q 11/00 | (2006.01) |

(52) U.S. Cl.
CPC .............. *A61K 8/22* (2013.01); *A61C 19/066* (2013.01); *A61K 6/0017* (2013.01); *A61K 6/0023* (2013.01); *A61K 6/0058* (2013.01); *A61K 6/0094* (2013.01); *A61K 8/0208* (2013.01); *A61K 8/042* (2013.01); *A61K 8/731* (2013.01); *A61K 8/817* (2013.01); *A61K 8/8152* (2013.01); *A61K 8/8176* (2013.01); *A61K 8/86* (2013.01); *A61L 15/60* (2013.01); *A61Q 11/00* (2013.01); *A61Q 11/02* (2013.01); *A61K 2800/262* (2013.01); *A61K 2800/54* (2013.01); *A61K 2800/5422* (2013.01); *A61K 2800/5424* (2013.01); *A61K 2800/59* (2013.01); *C08L 2312/00* (2013.01)

(58) Field of Classification Search
CPC ................ A61K 6/0017; A61K 6/0023; A61K 2800/262; A61K 2800/54; A61K 2800/5422; A61K 2800/5424; A61K 2800/59; A61K 6/0058; A61K 6/0094; A61K 8/0208; A61K 8/042; A61K 8/22; A61K 8/731; A61K 8/8152; A61K 8/817; A61K 8/8176; A61K 8/86; A61Q 11/02; A61Q 11/00; A61C 19/066; A61L 15/60
See application file for complete search history.

(56) References Cited

U.S. PATENT DOCUMENTS

| | | | |
|---|---|---|---|
| 2,561,071 | A | 7/1951 | Prisk |
| 2,579,403 | A | 12/1951 | Slomowitz et al. |
| 3,150,977 | A | 9/1964 | Hart et al. |
| 3,689,439 | A | 9/1972 | Field et al. |
| 3,721,657 | A | 3/1973 | Seiderman |
| 3,749,755 | A | 7/1973 | Bronstart et al. |

(Continued)

FOREIGN PATENT DOCUMENTS

| | | |
|---|---|---|
| CA | 2520986 | 4/2000 |
| CA | 2402021 | 9/2001 |

(Continued)

OTHER PUBLICATIONS

U.S. Appl. No. 11/150,811, filed Jun. 10, 2005, Feldstein et al.

(Continued)

*Primary Examiner* — Snigdha Maewall
(74) *Attorney, Agent, or Firm* — McDermott Will & Emery LLP

(57) ABSTRACT

A composition is provided, wherein the composition comprises a water-swellable, water insoluble polymer, a blend of a hydrophilic polymer and a complementary oligomer capable of hydrogen bonding to the hydrophilic polymer, and a whitening agent, preferably a peroxide. The composition finds utility as a tooth whitening composition and is applied to the teeth in need of whitening, and then removed when the degree of whitening has been achieved. In certain embodiments, the composition is translucent. Methods for preparing and using the compositions are also disclosed.

20 Claims, No Drawings

(56) References Cited

U.S. PATENT DOCUMENTS

| | | |
|---|---|---|
| 3,852,228 A | 12/1974 | Brothers |
| 3,957,605 A | 5/1976 | Assarsson et al. |
| 3,993,551 A | 11/1976 | Assarsson et al. |
| 3,996,934 A | 12/1976 | Zaffaroni |
| 4,091,090 A | 5/1978 | Sipos |
| 4,093,673 A | 6/1978 | Chang et al. |
| 4,160,020 A | 7/1979 | Ayer et al. |
| 4,231,369 A | 11/1980 | Sorensen et al. |
| 4,277,580 A | 7/1981 | Allen et al. |
| 4,325,851 A | 4/1982 | Colon et al. |
| 4,346,709 A | 8/1982 | Schmitt et al. |
| 4,367,732 A | 1/1983 | Poulsen et al. |
| 4,369,229 A | 1/1983 | Shah |
| 4,492,685 A | 1/1985 | Keith et al. |
| 4,529,601 A | 7/1985 | Broberg et al. |
| 4,537,776 A | 8/1985 | Cooper |
| 4,552,751 A | 11/1985 | Inaba et al. |
| 4,557,934 A | 12/1985 | Cooper |
| 4,562,060 A | 12/1985 | Broberg et al. |
| 4,568,343 A | 2/1986 | Leeper et al. |
| 4,587,289 A | 5/1986 | Comert et al. |
| 4,593,053 A | 6/1986 | Jevne et al. |
| 4,624,665 A | 11/1986 | Nuwayser |
| 4,699,146 A | 10/1987 | Sieverding |
| 4,713,243 A | 12/1987 | Schiraldi et al. |
| 4,743,249 A | 5/1988 | Loveland |
| 4,750,482 A | 6/1988 | Sieverding |
| 4,771,105 A | 9/1988 | Shirai et al. |
| 4,849,224 A | 7/1989 | Chang et al. |
| 4,863,738 A | 9/1989 | Taskovich |
| 4,863,970 A | 9/1989 | Patel et al. |
| 4,867,748 A | 9/1989 | Samuelsen |
| 4,871,536 A | 10/1989 | Arraudeau et al. |
| 4,873,299 A | 10/1989 | Nowakowsky et al. |
| 4,877,628 A | 10/1989 | Stypula |
| 4,904,247 A | 2/1990 | Therriault et al. |
| 4,906,169 A | 3/1990 | Chien et al. |
| 4,920,158 A | 4/1990 | Murray et al. |
| 4,927,408 A | 5/1990 | Haak et al. |
| 4,945,084 A | 7/1990 | Packman |
| 4,953,053 A | 8/1990 | Pratt |
| 4,973,468 A | 11/1990 | Chiang et al. |
| 4,983,395 A | 1/1991 | Chang et al. |
| 5,023,084 A | 6/1991 | Chien et al. |
| 5,053,227 A | 10/1991 | Chiang et al. |
| 5,057,500 A | 10/1991 | Thornfeldt |
| 5,073,381 A | 12/1991 | Ivan et al. |
| 5,102,662 A | 4/1992 | Gallagher |
| 5,125,894 A | 6/1992 | Phipps et al. |
| 5,133,970 A | 7/1992 | Petereit et al. |
| 5,141,750 A | 8/1992 | Lee et al. |
| 5,173,302 A | 12/1992 | Holmblad et al. |
| 5,183,901 A | 2/1993 | Login et al. |
| 5,196,405 A | 3/1993 | Packman |
| 5,200,190 A | 4/1993 | Azuma et al. |
| 5,206,385 A | 4/1993 | Login et al. |
| 5,224,928 A | 7/1993 | Sibalis et al. |
| 5,232,702 A | 8/1993 | Pfister et al. |
| 5,234,690 A | 8/1993 | Chiang et al. |
| 5,234,957 A | 8/1993 | Mantelle |
| 5,240,995 A | 8/1993 | Gyory et al. |
| 5,254,346 A | 10/1993 | Tucker et al. |
| 5,270,358 A | 12/1993 | Asmus |
| 5,276,079 A | 1/1994 | Duan et al. |
| 5,296,512 A | 3/1994 | Beier et al. |
| 5,300,291 A | 4/1994 | Sablotsky et al. |
| 5,310,563 A | 5/1994 | Curtis et al. |
| 5,322,689 A | 6/1994 | Hughes et al. |
| 5,326,685 A | 7/1994 | Gaglio et al. |
| 5,332,576 A | 7/1994 | Mantelle |
| 5,338,490 A | 8/1994 | Dietz et al. |
| 5,342,623 A | 8/1994 | Enscore et al. |
| 5,344,394 A | 9/1994 | Gyory et al. |
| 5,354,823 A | 10/1994 | Tseng et al. |
| 5,362,420 A | 11/1994 | Itoh et al. |
| 5,376,377 A | 12/1994 | Gale et al. |
| 5,422,119 A | 6/1995 | Casper |
| 5,438,076 A | 8/1995 | Friedman et al. |
| 5,446,070 A | 8/1995 | Mantelle |
| 5,456,745 A | 10/1995 | Roreger et al. |
| 5,462,743 A | 10/1995 | Turner et al. |
| 5,462,745 A | 10/1995 | Enscore et al. |
| 5,492,943 A | 2/1996 | Stempel |
| 5,508,024 A | 4/1996 | Tranner |
| 5,508,367 A | 4/1996 | Zajaczkowski |
| 5,527,271 A | 6/1996 | Shah et al. |
| 5,543,148 A | 8/1996 | Lapidus |
| 5,563,153 A | 10/1996 | Mueller et al. |
| 5,575,654 A | 11/1996 | Fontenot |
| 5,593,686 A | 1/1997 | Kissel et al. |
| 5,594,068 A | 1/1997 | Buchanan et al. |
| 5,599,373 A | 2/1997 | Zanuccoli |
| 5,614,178 A | 3/1997 | Bloon et al. |
| 5,614,586 A | 3/1997 | Tang et al. |
| 5,631,267 A | 5/1997 | Gleich et al. |
| 5,633,010 A | 5/1997 | Chen |
| 5,641,504 A | 6/1997 | Lee et al. |
| 5,641,507 A | 6/1997 | DeVillez |
| 5,643,187 A | 7/1997 | Naestoft et al. |
| 5,645,062 A | 7/1997 | Anderson et al. |
| 5,645,855 A | 7/1997 | Lorenz |
| 5,656,286 A | 8/1997 | Miranda et al. |
| 5,660,178 A | 8/1997 | Kantner et al. |
| 5,662,925 A | 9/1997 | Ebert et al. |
| 5,663,010 A | 9/1997 | Stocchiero |
| 5,674,561 A | 10/1997 | Dietz et al. |
| 5,700,478 A | 12/1997 | Biegajski et al. |
| 5,702,721 A | 12/1997 | Horstmann et al. |
| 5,718,187 A | 2/1998 | Pollock et al. |
| 5,718,886 A | 2/1998 | Pellico |
| 5,719,197 A | 2/1998 | Kanios et al. |
| 5,723,145 A | 3/1998 | Shikinami et al. |
| 5,725,876 A | 3/1998 | Mantelle et al. |
| 5,726,250 A | 3/1998 | Zajaczkowski |
| 5,730,999 A | 3/1998 | Lehmann et al. |
| 5,744,155 A | 4/1998 | Friedman et al. |
| 5,762,956 A | 6/1998 | Chien |
| 5,770,220 A | 6/1998 | Meconi et al. |
| 5,773,490 A | 6/1998 | Shikinami et al. |
| 5,780,050 A | 7/1998 | Jain et al. |
| 5,785,527 A | 7/1998 | Jensen et al. |
| 5,785,976 A | 7/1998 | Westesen et al. |
| 5,788,983 A | 8/1998 | Chien et al. |
| 5,800,832 A | 9/1998 | Tapolsky et al. |
| 5,804,611 A | 9/1998 | Takoh et al. |
| 5,827,213 A | 10/1998 | Jensen |
| 5,827,525 A | 10/1998 | Liao et al. |
| 5,830,932 A | 11/1998 | Kay |
| 5,837,713 A | 11/1998 | Gliech et al. |
| 5,843,472 A | 12/1998 | Ma et al. |
| 5,846,558 A | 12/1998 | Nielsen et al. |
| 5,851,549 A | 12/1998 | Svec |
| 5,853,755 A | 12/1998 | Foldvari |
| 5,857,992 A | 1/1999 | Haak et al. |
| 5,858,332 A | 1/1999 | Jensen et al. |
| 5,858,410 A | 1/1999 | Muller et al. |
| 5,863,662 A | 1/1999 | Hornby et al. |
| 5,876,746 A | 3/1999 | Jona et al. |
| 5,879,691 A | 3/1999 | Sagel et al. |
| 5,879,701 A | 3/1999 | Audett et al. |
| 5,891,453 A | 4/1999 | Sagel et al. |
| 5,894,017 A | 4/1999 | Sagel et al. |
| 5,900,249 A | 5/1999 | Smith |
| 5,902,598 A | 5/1999 | Chen et al. |
| 5,911,980 A | 6/1999 | Samour et al. |
| 5,912,271 A | 6/1999 | Brodine et al. |
| 5,916,587 A | 6/1999 | Min et al. |
| 5,942,543 A | 8/1999 | Ernst |
| 5,945,032 A | 8/1999 | Breitenbach et al. |
| 5,945,457 A | 8/1999 | Plate et al. |
| 5,948,416 A | 9/1999 | Wagner et al. |
| 5,948,430 A | 9/1999 | Zerbe et al. |
| 5,948,433 A | 9/1999 | Burton et al. |
| 5,958,379 A | 9/1999 | Regenold et al. |

(56) References Cited

U.S. PATENT DOCUMENTS

| | | |
|---|---|---|
| 5,958,446 A | 9/1999 | Miranda et al. |
| 5,958,984 A | 9/1999 | Devillez |
| 5,962,011 A | 10/1999 | DeVillez |
| 5,972,377 A | 10/1999 | Jona et al. |
| 5,976,565 A | 11/1999 | Fotinos |
| 5,985,311 A | 11/1999 | Cordes et al. |
| 5,985,860 A | 11/1999 | Toppo |
| 5,985,990 A | 11/1999 | Kantner et al. |
| 5,989,569 A | 11/1999 | Dirksing et al. |
| 5,990,179 A | 11/1999 | Gyori et al. |
| 5,993,836 A | 11/1999 | Castillo |
| 5,993,849 A | 11/1999 | Assmus et al. |
| 5,997,886 A | 12/1999 | Peffly et al. |
| 6,004,566 A | 12/1999 | Friedman et al. |
| 6,004,578 A | 12/1999 | Lee et al. |
| 6,007,837 A | 12/1999 | Enscore et al. |
| 6,024,976 A | 2/2000 | Miranda et al. |
| 6,045,811 A | 4/2000 | Dirksing et al. |
| 6,051,609 A | 4/2000 | Yu et al. |
| 6,063,399 A | 5/2000 | Assmus et al. |
| 6,068,650 A | 5/2000 | Hofmann et al. |
| 6,072,100 A | 6/2000 | Mooney et al. |
| 6,075,626 A | 6/2000 | Mizutani et al. |
| 6,083,421 A | 7/2000 | Huang et al. |
| 6,093,328 A | 7/2000 | Santina |
| 6,096,328 A | 8/2000 | Sagel et al. |
| 6,135,126 A | 10/2000 | Joshi |
| 6,142,939 A | 11/2000 | Eppstein et al. |
| 6,146,654 A | 11/2000 | Kubo |
| 6,153,215 A | 11/2000 | Samuelsen et al. |
| 6,162,456 A | 12/2000 | Dunbar et al. |
| 6,165,499 A | 12/2000 | Kleinsorgen et al. |
| 6,177,096 B1 | 1/2001 | Zerbe et al. |
| 6,193,993 B1 | 2/2001 | Murahashi et al. |
| 6,197,331 B1 | 3/2001 | Lerner et al. |
| 6,201,164 B1 | 3/2001 | Wulff et al. |
| 6,212,671 B1 | 4/2001 | Kanehira et al. |
| 6,221,341 B1 | 4/2001 | Montgomery |
| 6,221,383 B1 | 4/2001 | Miranda et al. |
| 6,231,885 B1 | 5/2001 | Carrara |
| 6,248,363 B1 | 6/2001 | Patel et al. |
| 6,264,981 B1 | 7/2001 | Zhang et al. |
| 6,270,792 B1 | 8/2001 | Guillemet et al. |
| 6,275,728 B1 | 8/2001 | Venkatraman et al. |
| 6,306,370 B1 | 10/2001 | Jensen et al. |
| 6,312,666 B1 | 11/2001 | Oxman et al. |
| 6,312,670 B1 | 11/2001 | Montgomery |
| 6,316,022 B1 | 11/2001 | Mantelle et al. |
| 6,322,774 B1 | 11/2001 | Jensen et al. |
| 6,329,472 B1 | 12/2001 | Kim et al. |
| 6,368,576 B1 | 4/2002 | Jensen et al. |
| 6,419,905 B1 | 7/2002 | Alvarez Hernandez |
| 6,419,906 B1 | 7/2002 | Xu et al. |
| 6,451,240 B1 | 9/2002 | Sherman et al. |
| 6,451,777 B1 | 9/2002 | Bradbury et al. |
| 6,461,636 B1 | 10/2002 | Arth et al. |
| 6,488,913 B2 | 12/2002 | Orlowski et al. |
| 6,517,350 B2 | 2/2003 | Diasti et al. |
| 6,552,147 B2 | 4/2003 | Parker et al. |
| 6,558,654 B2 | 5/2003 | McLaughlin |
| 6,562,363 B1 | 5/2003 | Mantelle et al. |
| 6,576,712 B2 | 6/2003 | Feldstein et al. |
| 6,585,997 B2 | 7/2003 | Moro et al. |
| 6,591,124 B2 | 7/2003 | Sherman et al. |
| 6,596,298 B2 | 7/2003 | Leung et al. |
| 6,602,912 B2 | 8/2003 | Hsu et al. |
| 6,611,706 B2 | 8/2003 | Avrahami et al. |
| 6,638,528 B1 | 10/2003 | Kanios |
| 6,656,493 B2 | 12/2003 | Dzija |
| 6,667,410 B2 | 12/2003 | Magnus et al. |
| 6,673,363 B2 | 1/2004 | Luo et al. |
| 6,682,721 B2 | 1/2004 | Kim et al. |
| 6,689,344 B2 | 2/2004 | Chang et al. |
| 6,696,459 B1 | 2/2004 | Jones et al. |
| 6,708,060 B1 | 3/2004 | Avrahami et al. |
| 6,709,671 B2 | 3/2004 | Zerbe et al. |
| 6,711,435 B2 | 3/2004 | Avrahami |
| 6,714,497 B2 | 3/2004 | Yeo et al. |
| 6,750,291 B2 | 6/2004 | Kim et al. |
| 6,759,030 B2 | 7/2004 | Kosti |
| 6,762,202 B2 | 7/2004 | Marek et al. |
| 6,780,401 B2 | 8/2004 | Kim et al. |
| 6,783,769 B1 | 8/2004 | Arth et al. |
| 6,803,420 B2 | 10/2004 | Cleary et al. |
| 6,805,874 B1 | 10/2004 | Lutz et al. |
| 6,806,308 B2 | 10/2004 | Zajac |
| 6,884,833 B2 | 4/2005 | Cheang et al. |
| 6,946,142 B2 | 9/2005 | Chang et al. |
| 6,962,691 B1 | 11/2005 | Lulla et al. |
| 7,078,359 B2 | 7/2006 | Stepanian et al. |
| 7,112,713 B2 | 9/2006 | Sceusa |
| 7,122,199 B2 | 10/2006 | Sagel et al. |
| 7,138,458 B2 | 11/2006 | Cleary et al. |
| 7,217,853 B2 | 5/2007 | Kulichikhin et al. |
| 7,323,161 B2 | 1/2008 | Choi et al. |
| 7,384,650 B2 | 6/2008 | Chien |
| 7,456,331 B2 | 11/2008 | Kulichikhin et al. |
| 7,744,918 B2 | 6/2010 | Yamaguchi et al. |
| 8,206,738 B2 | 6/2012 | Singh et al. |
| 8,273,405 B2 | 9/2012 | Feldstein et al. |
| 8,481,059 B2 | 7/2013 | Cleary et al. |
| 8,481,071 B2 | 7/2013 | Singh et al. |
| 8,541,021 B2 | 9/2013 | Singh et al. |
| 8,617,647 B2 | 12/2013 | Feldstein et al. |
| 8,658,201 B2 | 2/2014 | Singh et al. |
| 8,728,445 B2 | 5/2014 | Cleary et al. |
| 8,741,331 B2 | 6/2014 | Singh et al. |
| 8,753,669 B2 | 6/2014 | Cleary et al. |
| 8,784,879 B2 | 7/2014 | Singh et al. |
| 8,821,901 B2 | 9/2014 | Feldstein et al. |
| 8,840,918 B2 | 9/2014 | Singh et al. |
| 9,084,723 B2 | 7/2015 | Singh et al. |
| 9,089,481 B2 | 7/2015 | Singh et al. |
| 2001/0006677 A1 | 7/2001 | Mcginity et al. |
| 2001/0021374 A1 | 9/2001 | Montgomery |
| 2001/0022964 A1 | 9/2001 | Leung et al. |
| 2001/0046471 A1 | 11/2001 | Marek et al. |
| 2001/0046511 A1 | 11/2001 | Zerbe et al. |
| 2002/0004065 A1 | 1/2002 | Kanios |
| 2002/0004190 A1 | 1/2002 | Diasti et al. |
| 2002/0006387 A1 | 1/2002 | Sagel et al. |
| 2002/0009420 A1 | 1/2002 | McLaughlin |
| 2002/0032240 A1 | 3/2002 | Hsu et al. |
| 2002/0048602 A1 | 4/2002 | Flore et al. |
| 2002/0058936 A1 | 5/2002 | Avrahami et al. |
| 2002/0076487 A1 | 6/2002 | Zajac |
| 2002/0094426 A1 | 7/2002 | Stepanian et al. |
| 2002/0106335 A1 | 8/2002 | Orlowski et al. |
| 2002/0120170 A1 | 8/2002 | Magnus et al. |
| 2002/0131990 A1 | 9/2002 | Barkalow et al. |
| 2002/0169411 A1 | 11/2002 | Sherman et al. |
| 2002/0197284 A1 | 12/2002 | Luo et al. |
| 2003/0035841 A1 | 2/2003 | Dzija |
| 2003/0044446 A1 | 3/2003 | Moro et al. |
| 2003/0055190 A1 | 3/2003 | Parker et al. |
| 2003/0059381 A1 | 3/2003 | Goodhart et al. |
| 2003/0067855 A1 | 4/2003 | Yeo et al. |
| 2003/0068376 A1 | 4/2003 | Chen et al. |
| 2003/0082114 A1 | 5/2003 | Kim et al. |
| 2003/0097127 A1 | 5/2003 | Avrahami |
| 2003/0100654 A1 | 5/2003 | Cheang et al. |
| 2003/0101507 A1 | 6/2003 | Cleary et al. |
| 2003/0103427 A1 | 6/2003 | Yeo et al. |
| 2003/0104041 A1 | 6/2003 | Hsu et al. |
| 2003/0130427 A1 | 7/2003 | Cleary et al. |
| 2003/0133884 A1 | 7/2003 | Chang et al. |
| 2003/0152528 A1 | 8/2003 | Singh et al. |
| 2003/0152615 A1 | 8/2003 | Houze |
| 2003/0170308 A1 | 9/2003 | Cleary et al. |
| 2003/0180229 A1 | 9/2003 | Kosti |
| 2003/0194382 A1 | 10/2003 | Chang et al. |
| 2003/0199644 A1 | 10/2003 | Choi |
| 2003/0225356 A1 | 12/2003 | Kulichikhin et al. |
| 2003/0235549 A1 | 12/2003 | Singh et al. |

(56) References Cited

U.S. PATENT DOCUMENTS

| | | |
|---|---|---|
| 2004/0005277 A1 | 1/2004 | Willison et al. |
| 2004/0053901 A1 | 3/2004 | Chien |
| 2004/0105834 A1 | 6/2004 | Singh et al. |
| 2004/0136927 A1 | 7/2004 | Kim et al. |
| 2004/0166147 A1 | 8/2004 | Lundy et al. |
| 2004/0181183 A1 | 9/2004 | Sceusa |
| 2004/0186132 A1 | 9/2004 | Jones et al. |
| 2004/0213744 A1 | 10/2004 | Lulla et al. |
| 2004/0219111 A1 | 11/2004 | Kim et al. |
| 2004/0219113 A1 | 11/2004 | Choi et al. |
| 2004/0230227 A1 | 11/2004 | Avrahami et al. |
| 2004/0258723 A1 | 12/2004 | Singh et al. |
| 2005/0031554 A1 | 2/2005 | Kim et al. |
| 2005/0049365 A1 | 3/2005 | Cleary et al. |
| 2005/0113510 A1 | 5/2005 | Feldstein et al. |
| 2005/0208110 A1 | 9/2005 | Singh et al. |
| 2005/0215727 A1 | 9/2005 | Feldstein et al. |
| 2005/0228113 A1 | 10/2005 | Baumer et al. |
| 2005/0251088 A1 | 11/2005 | Kwon |
| 2005/0256223 A1 | 11/2005 | Kolb et al. |
| 2006/0034905 A1 | 2/2006 | Singh et al. |
| 2006/0089674 A1 | 4/2006 | Walters et al. |
| 2006/0110434 A1 | 5/2006 | Yamaguchi et al. |
| 2006/0168905 A1 | 8/2006 | Blanc et al. |
| 2006/0171906 A1 | 8/2006 | Singh et al. |
| 2006/0182788 A1 | 8/2006 | Singh et al. |
| 2006/0193793 A1 | 8/2006 | Kim et al. |
| 2006/0193794 A1 | 8/2006 | Kim et al. |
| 2006/0257463 A1 | 11/2006 | Elsohly et al. |
| 2007/0051376 A1 | 3/2007 | Kulichikhin et al. |
| 2008/0161492 A1 | 7/2008 | Cleary et al. |
| 2009/0155343 A1 | 6/2009 | Kawahara et al. |
| 2009/0258060 A1 | 10/2009 | Cleary et al. |
| 2010/0239644 A1 | 9/2010 | Feldstein et al. |
| 2010/0291186 A1 | 11/2010 | Singh et al. |
| 2012/0027695 A1 | 2/2012 | Feldstein et al. |
| 2012/0237579 A1 | 9/2012 | Singh et al. |
| 2012/0321569 A1 | 12/2012 | Feldstein et al. |
| 2013/0261526 A1 | 10/2013 | Cleary et al. |
| 2013/0273127 A1 | 10/2013 | Singh et al. |
| 2014/0044650 A1 | 2/2014 | Singh et al. |
| 2014/0147489 A1 | 5/2014 | Singh et al. |
| 2014/0271781 A1 | 9/2014 | Singh et al. |
| 2014/0322143 A1 | 10/2014 | Feldstein et al. |
| 2014/0322284 A1 | 10/2014 | Singh et al. |
| 2014/0371692 A1 | 12/2014 | Cleary et al. |
| 2015/0080437 A1 | 3/2015 | Lee et al. |
| 2015/0139919 A1 | 5/2015 | Singh et al. |

FOREIGN PATENT DOCUMENTS

| | | |
|---|---|---|
| CA | 2451431 | 1/2003 |
| CA | 2506073 | 6/2004 |
| CA | 2515128 A1 | 8/2004 |
| CA | 2579492 | 3/2006 |
| DE | 8509793 | 5/1985 |
| DE | 4219368 | 6/1992 |
| DE | 19745208 A1 | 4/1999 |
| EP | 0184470 | 6/1986 |
| EP | 0303445 | 2/1989 |
| EP | 0364211 | 4/1990 |
| EP | 0371421 | 6/1990 |
| EP | 0511782 | 11/1992 |
| EP | 0516026 | 12/1992 |
| EP | 0545594 | 6/1993 |
| EP | 0581581 | 2/1994 |
| EP | 0672094 | 9/1995 |
| EP | 0737477 | 10/1996 |
| EP | 0838225 | 4/1998 |
| EP | 0848960 | 6/1998 |
| EP | 1066823 | 1/2001 |
| EP | 2005952 A1 | 12/2008 |
| EP | 2196197 A1 | 6/2010 |
| GB | 1108837 | 4/1968 |
| JP | 58-162681 | 9/1983 |
| JP | 59-196817 | 11/1984 |
| JP | 01-151524 A | 6/1989 |
| JP | 03-066612 | 3/1991 |
| JP | 03-247334 | 5/1991 |
| JP | 03-275619 | 6/1991 |
| JP | 04-266818 | 9/1992 |
| JP | 06-100467 | 4/1994 |
| JP | 08-092080 A | 9/1994 |
| JP | 10-017448 | 1/1998 |
| JP | 2001-213768 A | 7/2001 |
| JP | 2002-029949 | 1/2002 |
| JP | 2002-145746 A | 5/2002 |
| KR | 20020045224 | 6/2002 |
| KR | 20030000299 | 1/2003 |
| KR | 20030000528 | 1/2003 |
| KR | 20030003969 | 1/2003 |
| KR | 20030003973 | 1/2003 |
| SU | 1459215 | 11/1995 |
| WO | WO 89/03859 | 5/1989 |
| WO | WO 90/07940 A1 | 7/1990 |
| WO | WO 93/02717 | 2/1993 |
| WO | WO 94/05340 | 3/1994 |
| WO | WO 96/19205 | 6/1996 |
| WO | WO 96/40047 A1 | 12/1996 |
| WO | WO 97/11676 | 4/1997 |
| WO | WO 98/20862 A1 | 5/1998 |
| WO | WO 98/26763 A1 | 6/1998 |
| WO | WO 98/37870 | 9/1998 |
| WO | WO 98/55044 | 12/1998 |
| WO | WO 99/11728 A1 | 3/1999 |
| WO | WO 99/17738 | 4/1999 |
| WO | WO 99/44678 | 9/1999 |
| WO | WO 99/47128 | 9/1999 |
| WO | WO 99/54422 | 10/1999 |
| WO | WO 99/65312 A2 | 11/1999 |
| WO | WO 00/16725 | 3/2000 |
| WO | WO 00/18365 A2 | 4/2000 |
| WO | WO 00/61120 A1 | 10/2000 |
| WO | WO 00/69421 | 11/2000 |
| WO | WO 01/01958 | 1/2001 |
| WO | WO 01/07018 A1 | 2/2001 |
| WO | WO 01/26637 | 4/2001 |
| WO | WO 01/68045 | 9/2001 |
| WO | WO 01/87276 | 11/2001 |
| WO | WO 02/00182 A3 | 1/2002 |
| WO | WO 02/04570 | 1/2002 |
| WO | WO 02/43657 A2 | 6/2002 |
| WO | WO 02/087642 | 11/2002 |
| WO | WO 02/087645 | 11/2002 |
| WO | WO 02/089849 | 11/2002 |
| WO | WO 03/000216 | 1/2003 |
| WO | WO 03/011259 A1 | 2/2003 |
| WO | WO 03/015748 A2 | 2/2003 |
| WO | WO 03/089046 | 10/2003 |
| WO | WO 03/099344 | 12/2003 |
| WO | WO 03/101357 | 12/2003 |
| WO | WO 2004/000389 A2 | 12/2003 |
| WO | WO 2004/024224 A1 | 3/2004 |
| WO | WO 2004/045569 | 6/2004 |
| WO | WO 2004/054638 | 7/2004 |
| WO | WO 2004/071323 | 8/2004 |
| WO | WO 2004/093786 | 11/2004 |
| WO | WO 2004/103201 | 12/2004 |
| WO | WO 2005/027768 | 3/2005 |
| WO | WO 2005/074894 A1 | 8/2005 |
| WO | WO 2006/017807 | 2/2006 |
| WO | WO 2006/029407 | 3/2006 |
| WO | WO 2006/069236 | 6/2006 |
| WO | WO 2006/074173 | 7/2006 |
| WO | WO 2006/081497 | 8/2006 |
| WO | WO 2006/124639 | 11/2006 |
| WO | WO 2007/119656 | 10/2007 |
| WO | WO 2010/083035 | 7/2010 |

OTHER PUBLICATIONS

U.S. Appl. No. 12/687,586, filed Jan. 11, 2009, Singh et al.
"Aquasorbe® A-500 Cellulose Gum (CMC)", Hercules Incorporated, Aqualon Division, Product Data No. 4234, 2 pgs. (2005).

(56) References Cited

OTHER PUBLICATIONS

Aubin et al., "Analysis of the glass transition temperature of miscible polymer blends", Macromolecules, vol. 21, pp. 2945-2949, (1988).
Bairamov et al., "Kinetic parameters of poly(N-vinyl pyrrolidone) spontaneous mixing with short-chain poly(ethylene glycol)", Polym. Mater. Sci. Eng., vol. 82, pp. 7-8, (2000).
Barbucci et al. "Swelling behavior of carboxymethylcellulose hydrogels in relation to cross-linking, pH, and charge density", Macromolecules, vol. 33, No. 20, pp. 7475-7480 (2000).
Borodulina et al. "Viscoelasticity of Pressure-sensitive adhesive and bioadhesive hydrogels under compressive load", Proceed. 24th Annual Meeting Adhesion Soc., pp. 147-149, (2001).
Chalykh et al., "Effects of composition and hydration on adhesive properties of poly(N-vinyl pyrrolidone)-poly(ethylene glycol) hydrogels", Polym. Mater. Sci. Eng., vol. 81, pp. 456-457, (1999).
Chalykh et al., "Fracture mechanics of poly(N-vinyl pyrrolidone)-poly(ethylene glycol) hydrogel adhesive joints," Polym. Mater. Sci. Eng., vol. 81, pp. 427-428, (1999).
Chalykh et al., "Pressure-sensitive adhesion in the blends of poly(N-vinyl pyrrolidone) and poly(ethylene glycol) of disparate chain lengths," J. Adhesion, vol. 78, pp. 667-694, (2002).
Cleary et al., A new polymer blend adhesive with combined properties to adhere to either skin or mucosa for drug delivery, podium abstract, 30th Annual Meeting and Exposition of the Controlled Release Society, Glasgow, Scotland, Jul. 19-23, 2003, Abstract #123.
Database WPI Section Ch, Week 198451, Derwent Publications Ltd., London, GB; Class A96, An 1984-315114 & JP 59196817 A (Sekisuki Chem Ind Co Ltd) Nov. 8, 1984 (Nov. 8, 1984) abstract.
Database WPI Section Ch, Week 199150, Derwent Publications Ltd., London, GB; Class A18, An 1991-366353 & JP 03247334 A (Sumitomo Rubber Ind Ltd) Nov. 5, 1991 (Nov. 5, 1991) abstract.
Database WPI Section Ch, Week 199118, Derwent Publications Ltd., London, GB; Class A96, An 1991-128478 & JP 03066612 A (Sato Pharm Co Ltd) Mar. 22, 1991 (Mar. 22, 1991) abstract.
Database WPI Section Ch, Week 199627, Derwent Publications Ltd., London, GB; Class A14, An 1996-266746 & SU 1459215 A ( A Med Cardiology Res Centre) Nov. 20, 1995 (Nov. 20, 1995) abstract.
Emla Cream, (lidocaine 2.5% and prilocaine 2.5%), EMLA Anesthetic Disc, (lidocaine 2.5% and prilocaine 2.5% cream), "Topical anesthetic for dermal analgesia", AstraZeneca Product Monograph, 46 pgs, Revised May 25, 2010.
Feldstein et al., "A structure—property relationship and quantitative approach to the development of universal transdermal drug delivery system," NBC Risks, vol. 25, pp. 441-458, (1999).
Feldstein et al., "Coherence of thermal transitions in poly(N-vinyl pyrrolidone)—poly(ethylene glycol) compatible blends: 1. Interrelations among the temperatures of melting, maximum cold crystalization rate and glass transition", Polymer, vol. 41, pp. 5327-5338, (2000).
Feldstein et al., "Coherence of thermal transitions in poly(N-vinyl pyrrolidone)—poly(ethylene glycol) compatible blends: 2. The temperature of maximum cold crystalization rate versus glass transition", Polymer, vol. 41, pp. 5339-5348, (2000).
Feldstein et al., "Coherence of thermal transitions in poly(N-vinyl pyrrolidone)—poly(ethylene glycol) compatible blends: 3. Impact of sorbed water upon phase behavior", Polymer, vol. 41, pp. 5349-5359, (2000).
Feldstein et al., "Correlations between activation energy for debonding and that for self-diffusion in pressure-sensitive hydrogels", Proceed. 24th Annual Meeting Adhession Soc., pp. 137-140, (2001).
Feldstein et al., "Contribution of molecular mobility to debonding of pressure-sensitive adhesive hydrogels", Polym. Mater. Sci. Eng., vol. 81, pp. 467-468, (1999).
Feldstein et al., "Effect of hydrophilic matrix hydration on transdermal drug delivery kinetics: I. The matrix hydration In Vivo and In Vitro", Prediction of Percutaneous Penetration, vol. 4b, pp. 61-64, Brian, et al., (Eds.) (1996).
Feldstein et al., "Effect of hydrophilic matrix hydration on transdermal drug delivery kinetics: II. In Vitro cytasine Delivery From Cypercuten TTS", Prediction of Percutaneous Penetration, vol. 4b, pp. 65-67, Brian, et al., (Eds.) (1996).
Feldstein et al., "Effect of hydrophilic matrix hydration on transdermal drug delivery kinetics: III. In Vitro clonide delivery from clopercuten TTS", Prediction of Percutaneous Penetration, vol. 4b, pp. 68-70, Brian, et al., (Eds.) (1996).
Feldstein et al., "Effect of hydrophilic matrix hydration on transdermal drug delivery kinetics: IV. In Vitro—In Vivo correlation," Prediction of Percutaneous Penetration, vol. 4b, pp. 71-73, Brian, et al., (eds.) (1996).
Feldstein et al., "Effects of chains orientation, free volume and interaction on glass transition in poly(N-vinyl pyrrolidone)—poly(ethylene glycol) blends involving a stoichiometric hydrogen-B bonded network complex", Polym. Mater. Sci. Eng., vol. 82, pp. 365-366, (2000).
Feldstein et al., "General approach to the molecular design of hydrophilic pressure-sensitive adhesives," Proc. 25th Ann. Mtg. and 2nd World Congress on Adhesion and Related Phenomena, Orlando, FL, vol. 1, pp. 292-294 (2002).
Feldstein et al., "Molecular insight into rheological and diffusion determinants of pressure sensitive adhesion", Proceed. 23rd Annual Meeting Adhesion Soc., pp. 54-56, (2000).
Feldstein et al., "Peculiarities of glass transition temperature relation to the composition of poly(N-vinyl pyrrolidone) blends with short chain poly(ethylene glycd)", Polymer, vol. 42, pp. 7719-7726, (2001).
Feldstein et al., "Quantitative relationship between molecular structure and adhesion of PVP-PEG hydrogels", Polym. Mater. Sci Eng., vol. 81, pp. 465-466, (1999).
Feldstein et al., "Relation of glass transition temperature to the hydrogen bonding degree and energy in poly(N-vinyl pyrrolidone) blends with hydroxyl-containing plasticizers: 2. Effects of poly(ethylene glycol) chain length", Polymer, vol. 42, pp. 981-990, (2001).
Feldstein et al., "Universal hydrophilic drug-containing adhesive matrix for systemic and topical transdermal drug delivery", Proc. 1st World Meeting APGI/APV, Budapest, Sep. 2011, 2 pages, (1995).
Feldstein et al., "A new class of pressure-sensitive adhesives based on interpolymer and polymer-oligomer complexes", Polymer Science, vol. 51, No. 7, pp. 799-814 (2009).
Ghebre-Sellassie et al., "A unique application and characterization of Eudragit E 30 D film coatings in sustained release formulations", Int. J. Pharmaceutics, vol. 31, Issues 1-2, pp. 43-54 (1986) Abstract Only.
Handbook of Pharmaceutical Excipients, "Polymethacrylate", Arther H. Kibbe, ed., 3rd ed., pp. 401-406, (2000).
Hawley's Condensed Chemical Dictionary, 14th Edition, Citation, "Oligomer, A polymer molecule of only a few monomer units (dimer, trimer, tetramer)", John Wiley and Sons, Inc., (2002).
Hurkmans et al., "Skin irritation caused by transdermal drug delivery systems during long-term (5 days) application", Br. J. Dermatology, vol. 112, No. 4, pp. 461-467 (1985).
International Search Report for PCT/US2000/18557 mailed Oct. 17, 2000.
International Search Report for PCT/US2001/21417 mailed Feb. 25, 2002.
International Search Report for PCT/US2002/13680 mailed Sep. 18, 2002.
International Search Report for PCT/US2002/14260 Mailed Sep. 17, 2002.
International Search Report for PCT/US2002/14725 mailed Sep. 27, 2002.
International Search Report for PCT/US2003/16408 Mailed Dec. 8, 2003.
International Search Report for PCT/US2003/039717 Mailed Jun. 28, 2004.
International Search Report for PCT/US2004/003443 Mailed Aug. 20, 2004.

(56) References Cited

OTHER PUBLICATIONS

International Search Report for PCT/US2004/011567 Mailed Jan. 10, 2006.
International Search Report for PCT/US2004/015448 Mailed Dec. 28, 2004.
International Search Report for PCT/US2004/029620 Mailed Jun. 1, 2005.
International Search Report for PCT/US2005/0002873 Mailed Apr. 27, 2005.
International Search Report for PCT/US2005/0034439 Mailed Jul. 19, 2006.
International Search Report for PCT/US2005/0046577 Mailed Jul. 26, 2006.
International Search Report for PCT/US/2005/028063 Mailed Apr. 28, 2006.
International Search Report for PCT/US/2005/032525 Mailed Mar. 17, 2006.
International Search Report for PCT/US/2006/000098 Mailed Nov. 3, 2006.
International Search Report for PCT/US2006/0003091 Mailed Oct. 11, 2006.
International Search Report for PCT/US2006/018500 Mailed Sep. 21, 2006.
International Search Report for PCT/US2010/000081 Mailed Sep. 7, 2010.
International Search Report for PCT/US2014/056118 Mailed Feb. 11, 2015.
Kotomin et al., "Squeeze-recoil analysis of adhesive hydrogels and elastomers", Polym. Mater. Sci. Eng., vol. 81, pp. 425-426, (1999).
Kotomin et al., "Durability and fracture of some visceolastic adhesives," Proceed. of the 23rd Annual Meeting of the Adhesion Soc., pp. 413-415, (Feb. 20-23, 2000).
MSDS (Material Safety Data Sheet), Lactic Acid, No. L0522, (2008).
Patent Abstracts of Japan, vol. 017, No. 055 (C-I023) Feb. 3, 1993 (Feb. 3, 1993) & JP 04 266818 A (Sekisui Chem Co Ltd), Sep. 22, 1992 (Sep. 22, 1992) abstract.
Roos et al., "Probe tack investigation of poly(vinyl pyrrolidone)-poly(ethylene glycol) blends", Proceed. 24th Annual Meeting Adhesion Soc., pp. 277-279, (2001).
Schehlmann "Polyvinylcaprolactam: physical and cosmetic properties of a new hair fixative resin", Lecture held at the IN-Cosmetics, SOFW-Journal-Sounderdruck, Dusseldorf, 6 pages (1997).
Sintov et al., "Radiofrequency-driven skin microchanneling as a new way for electically assisted transdermal delivery of hydrophilic drugs", J. Contr.Release, vol. 89, pp. 311-320, (2003).
Supplementary European Search Report for EP04783729.9 Mailed Jun. 5, 2009.
Vartapian et al., "Self-diffusion in poly(N-vinyl pyrrolidone)-poly(ethylene glycol) systems", Colloid Polym. Sci., vol. 279, pp. 532-538, (2001).
Vartapian et al., "Molecular dynamics in poly(N-vinyl pyrrolidone)-poly(ethylene glycol) blends by pulsed-field gradient NMR method: effects of aging, hydration and PEG chain length", Macromol. Chem. Phys., vol. 202, pp. 2648-2652, (2001).
Whelan Polymer Technology Dictionary, Citation *Butyl Rubber*, Chapman Hall, 2-6 Boundry Row, London, UK, vol. 1, pp. 53 (1994).

HYDROGEL COMPOSITIONS FOR TOOTH WHITENING

CROSS-REFERENCE TO RELATED APPLICATIONS

This application is a continuation of U.S. patent application Ser. No. 14/494,304, filed Sep. 23, 2014, now allowed, which is a continuation of U.S. patent application Ser. No. 10/359,548, filed Feb. 5, 2003, now U.S. Pat. No. 8,840,918, which is a continuation-in-part of U.S. patent application Ser. No. 10/137,664, filed May 1, 2002, now U.S. Pat. No. 8,728,445, which claims priority under 35 U.S.C. §119(e)(1) to Provisional Patent Application No. 60/288,008, filed May 1, 2001, the contents each of which is incorporated herein in its entirety.

TECHNICAL FIELD

This invention relates generally to hydrogel compositions for dental care, and more particularly related to novel hydrogel compositions useful in the whitening of an individual's teeth.

BACKGROUND

Discoloration of the teeth occurs widely in society, and is estimated to occur in two out of three adults. Dental discoloration is considered an aesthetic flaw or defect, and can have negative consequences in an affected person's life by causing self-consciousness, and even inhibiting smiling. Tooth discoloration can be particularly distressing or troublesome in situations and professions where showing clean and white teeth is essential.

A tooth is comprised of an inner dentin layer and an outer hard enamel layer that is slightly porous. The outer layer is the protective layer of the tooth. The natural color of the tooth is opaque to translucent white or slightly off-white. Staining of teeth arises as a result of exposure of compounds such as tannins and other polyphenolic compounds to the teeth. These compounds become entrapped or bound to the proteinaceous layer on the surface of the teeth, and can penetrate the enamel and even the dentin. On occasion, staining can arise from sources within the tooth, such as tetracycline, which may become deposited in the teeth if administered to an individual when young.

Surface staining can usually be removed by mechanical tooth cleaning. However, discolored enamel or dentin is not amenable to mechanical methods of tooth cleaning, and chemical methods, which can penetrate into the tooth structure, are required to remove the stains. The most effective treatments for dental discoloration are compositions containing an oxidizing agent, such as hydrogen peroxide, that is capable of reacting with the chromogen molecules responsible for the discoloration, and rendering them either colorless or water-soluble, or both.

Consequently, tooth whitening compositions generally fall into two categories: (1) gels, pastes, or liquids, including toothpastes that are mechanically agitated at the stained tooth surface in order to affect tooth stain removal through abrasive erosion of surface stains; and (2) gels, pastes, or liquids that accomplish a tooth-bleaching effect by a chemical process while in contact with the stained tooth surface for a specified period, after which the formulation is removed. In some cases, an auxiliary chemical process, which may be oxidative or enzymatic, supplements the mechanical process.

Some dental compositions such as dentrifices, toothpastes, gels, and powders contain active oxygen or hydrogen peroxide liberating bleaching agents. Such bleaching agents include peroxides, percarbonates and perborates of the alkali and alkaline earth metals or complex compounds containing hydrogen peroxide. Also, peroxide salts of the alkali or alkaline earth metals are known to be useful in whitening teeth.

Of the many peroxides available to the formulator of tooth whitening compositions, hydrogen peroxide (and its adducts or association complexes, such as carbamide peroxide and sodium percarbonate) has been used almost exclusively. The chemistry of hydrogen peroxide is well known, although the specific nature of its interactions with tooth chromogens is poorly understood. It is believed that hydrogen peroxide destroys tooth chromogens by oxidizing unsaturated carbon-carbon, carbon-oxygen, and carbon-nitrogen bonds found in the stain molecules, thus rendering them colorless or soluble.

A related class of compound, the peroxyacids, has been used in laundry detergents to effectively whiten clothes, due primarily to their stability in solution and their specific binding abilities to certain types of stain molecules. A number of stable, solid peroxyacids have been used, including diperoxydodecanoic acid and the magnesium salt of monoperoxyphthalic acid. Other peroxyacids, such as peroxyacetic acid, are available as solutions containing an equilibrium distribution of acetic acid, hydrogen peroxide, peroxyacetic acid and water. Alternatively, a peroxide donor such as sodium perborate or sodium percarbonate is formulated together with a peroxyacid precursor. Upon contact with water, the peroxide donor releases hydrogen peroxide which then reacts with the peroxyacid precursor to form the actual peroxyacid. Examples of peroxyacids created in situ include peroxyacetic acid (from hydrogen peroxide and tetraacetylethylenediamine) and peroxynonanoic acid (from hydrogen peroxide and nonanoyloxybenzene sulfonate).

Peroxyacids have also been used in oral care compositions to whiten stained teeth. U.S. Pat. No. 5,279,816 describes a method of whitening teeth comprising the application of a peroxyacetic acid-containing composition having an acid pH. EP 545,594 A1 describes the use of peroxyacetic acid in preparing a composition for whitening teeth. The peroxyacetic acid may be present in the composition, or alternatively, may be generated in situ by combining a peroxide source with a peroxyacetic acid precursor during use. For example, U.S. Pat. No. 5,302,375 describes a composition that generates peroxyacetic acid within a vehicle in situ by combining water, acetylsalicylic acid and a water-soluble alkali metal percarbonate.

The most commonly used dental whitening agent is carbamide peroxide ($CO(NH_2)_2$ $H_2O_2$), also called urea hydrogen peroxide, hydrogen peroxide carbamide, and perhydrol-urea. Carbamide peroxide had been used by dental clinicians for several decades as an oral antiseptic, and tooth bleaching was an observed side effect of extended contact time. Over-the-counter compositions of 10% carbamide peroxide are available as GLY-OXIDE® by Marion Laboratories and PROXIGEL® by Reed and Carnrick, which are low-viscosity compositions that must be held in a tray or similar container in order to provide contact with the teeth. A bleaching gel which is able to hold a comfortable-fitting dental tray in position for an extended time period is available under the trademark OPALESCENCE® from Ultradent Products, Inc. in South Jordan, Utah.

In order for such compositions to stay in place, the compositions must be a viscous liquid or a gel. The use of dental trays also requires that the tray be adapted for comfort and fit so that the tray will not exert pressure or cause irritation to the person's teeth or gums. Such whitening compositions necessarily should be formulated so as to be sufficiently sticky and viscous to resist dilution by saliva.

In one method of whitening an individual's teeth, a dental professional will construct a custom made dental bleaching tray for the patient from an impression made of the patient's dentition and prescribe the use of an oxidizing gel to be dispensed into the bleaching tray and worn intermittently for a period of from about 2 weeks to about 6 months, depending upon the severity of tooth staining. These oxidizing compositions, usually packaged in small plastic syringes or tubes, are dispensed directly by the patient into the custom-made tooth-bleaching tray, held in place in the mouth for contact times of greater than about 60 minutes, and sometimes as long as 8 to 12 hours. The slow rate of bleaching is in large part the consequence of the very nature of formulations that are developed to maintain stability of the oxidizing composition.

For example. U.S. Pat. No. 6,368,576 to Jensen describes tooth whitening compositions that are preferably used with a tray so that the composition is held in position adjacent to the person's tooth surfaces to be treated. These compositions are described as a sticky matrix material formed by combining a sufficient quantity of a tackifying agent, such as carboxypolymethylene with a solvent, such as glycerin, polyethylene glycol, or water.

In another example, U.S. Pat. No. 5,718,886 to Pellico describes a tooth whitening composition in the form of a gel composition containing carbamide peroxide dispersed in an anhydrous gelatinous carrier, which includes a polyol, a thickener, and xanthan gum.

Yet another example is descried in U.S. Pat. No. 6,419,905 to Hernandez, which describes the use of compositions containing carbamide peroxide (0.3-60%), xylitol (0.5-50%), a potassium salt (0.001-10%) and a fluorine salt (0.15-3%), formulated into a gel that contains between 0.5 and 6% by weight of an appropriate gelling agent.

A tooth whitening composition that adheres to the teeth is described in U.S. Pat. Nos. 5,989,569 and 6,045,811 to Dirksing. According to these patents, the gel contains 30-85% glycerin or polyethylene glycol, 10-22% urea/hydrogen peroxide complex, 0-12% carboxypolymethylene, 0-1% sodium hydroxide, 0-100% triethanolamine (TEA), 0-40% water, 0-1% flavor, 0-15% sodium citrate, and 0-5% ethylenediaminetetraacetic acid. The preferred gel according to Dirksing has a viscosity between 200 and 1,000,000 cps at low shear rates (less than one 1/seconds), and is sufficiently adhesive so as to obviate the need for a tray.

Currently available tooth-bleaching compositions have a significant disadvantage in that they cause tooth sensitization in over 50% of patients. Tooth sensitivity may result from the movement of fluid through the dentinal tubules, which is sensed by nerve endings in the tooth, due to the presence of glycerin, propylene glycol and polyethylene glycol in these compositions. This can result in varying amounts of tooth sensitivity following exposure of the teeth to heat, cold, overly sweet substances, and other causative agents.

Prolonged exposure of teeth to bleaching compositions, as practiced at present, has a number of adverse effects in addition to that of tooth sensitivity. These adverse effects include leaching of calcium from the enamel layer at a pH less than 5.5; penetration of the intact enamel and dentin by the bleaching agents and risking damage to pulpal tissue; and dilution of the bleaching compositions with saliva resulting in leaching from the dental tray and subsequent ingestion by the user.

Some oxidizing compositions (generally having relatively high concentrations of oxidizers) are applied directly to the tooth surface of a patient in a dental office setting under the supervision of a dentist or dental hygienist. Theoretically, such tooth whitening strategies yield faster results and better overall patient satisfaction. However, due to the high concentration of oxidizing agents contained in these so called "in-office" compositions, they can be hazardous to the patient and practitioner alike if not handled with care. The patient's soft tissues (the gingiva, lips, and other mucosal surfaces) must first be isolated from potential exposure to the active oxidizing agent by the use of a perforated rubber sheet (known as a rubber dam), so that only the teeth protrude. Alternatively, the soft tissue may be isolated from the oxidizers to be used in the whitening process by covering the soft tissue with a polymerizable composition that is shaped to conform to the gingival contours and subsequently cured by exposure to a high intensity light source. Once the soft tissue has been isolated and protected, the practitioner may apply the oxidizing agent directly onto the stained tooth surfaces for a specified period of time or until a sufficient change in tooth color has occurred. Typical results obtained through the use of an in-office tooth whitener, range from about 2 to 3 shades (as measured with the VITA Shade Guide, VITA Zahnfarbik).

The range of tooth shades in the VITA Shade Guide varies from very light (B1) to very dark (C4). A total of 16 tooth shades constitute the entire range of colors between these two endpoints on a scale of brightness. Patient satisfaction with a tooth whitening procedure increases with the number of tooth shade changes achieved, with a generally accepted minimum change desirable of about 4 to 5 VITA shades.

It is desirable, with respect to dental care products for tooth whitening, to provide dental care products utilizing an adhesive hydrogel that includes a whitening agent for removing stains from an individual's teeth. Compositions are desired that do not require the use of dental trays to provide contact between the bleaching agent and the teeth. Such products ideally would cause minimal or no tooth sensitivity, would minimize or eliminate leakage of the whitening agent resulting in ingestion by the user or resulting in damage or irritation to the gums or mucous membranes of the mouth, would provide for longer wear duration, sustained dissolution of the tooth whitening agent, improved efficacy, and be well tolerated by patients. It would also be desirable to provide a tooth whitening dental care product that is a solid composition and self-adhesive but which does not stick to the fingers of the user, or that is a non-solid (e.g., liquid or gel) and which forms a film when dry. The instant invention addresses these needs.

SUMMARY OF THE INVENTION

One aspect of the invention relates to a composition comprising a water-swellable, water-insoluble polymer, a blend of a hydrophilic polymer and a complementary oligomer capable of hydrogen bonding or electrostatic bonding to the hydrophilic polymer, and a whitening agent.

In a preferred embodiment, the water-swellable, water-insoluble polymer is a cellulose ester, or an acrylate-based polymer or copolymer; the hydrophilic polymer is an poly (N-vinyl lactam), poly(N-vinyl amide), poly(N-alkylacrylamide), or copolymer and blend thereof; the complementary oligomer capable of hydrogen bonding to the hydrophilic polymer is a polyalkylene glycol or a carboxyl-terminated polyalkylene glycol; and the whitening agent is a peroxide.

The composition optionally comprises a low molecular weight plasticizer, and may also comprise at least one additive selected from the group consisting of fillers, preservatives, pH regulators, softeners, thickeners, colorants (e.g., pigments, dyes, refractive particles, etc.), flavorants (e.g., sweeteners, flavors), stabilizers, toughening agents and detackifiers.

In a preferred method of using the composition, the composition is a tooth whitening composition and is applied to the teeth in need of whitening, and then removed when the degree of whitening has been achieved. In certain embodiments, the tooth whitening composition is translucent, and the composition is removed when the user is satisfied with the degree of whitening achieved.

Yet another aspect of the invention pertains to a composition comprising a water-swellable, water-insoluble polymer, a blend of a hydrophilic polymer and a complementary oligomer capable of hydrogen bonding to the hydrophilic polymer, and an agent selected from the group consisting of peroxides, metal chlorites, perborates, percarbonates, peroxyacids, and combinations thereof.

Another aspect of the invention relates to a method for preparing a hydrogel film suitable for incorporation into a tooth whitening composition is provided. This method comprises preparing a solution or a gel of a water-swellable, water-insoluble polymer, a hydrophilic polymer, and a complementary oligomer capable of hydrogen bonding or electrostatic bonding to the hydrophilic polymer, in a solvent; depositing a layer of the solution on a substrate to provide a coating thereon; and heating the coated substrate to a temperature in the range of about 80° C. to about 100° C. for a time period in the range of about 1 to about 4 hours, thereby providing a hydrogel film on the substrate.

In another method of forming a tooth whitening composition, the method comprises melt processing through an extruder a mixture of a water-swellable, water-insoluble polymer, a hydrophilic polymer, and a complementary oligomer capable of hydrogen bonding or electrostatic bonding to the hydrophilic polymer, to form an extruded composition; wherein the composition is extruded as a film of desired thickness onto a suitable substrate.

The method further comprises loading the hydrogel film with the whitening agent, thereby providing the tooth whitening composition.

The adhesive tooth whitening compositions of the invention provide a number of significant advantages relative to the prior art. In particular, the present compositions:

(1) provide ease of handling;
(2) are readily modified during manufacture so that properties such as adhesion, absorption, translucence, and swelling can be controlled and optimized;
(3) can be formulated so that track increases or decreases in the presence of moisture so that the composition is not sticky until moistened;
(4) minimize leakage of the whitening agent from the composition into the user's mouth;
(5) can be fabricated in translucent from, enabling the user to view the extent of whitening without removing the hydrogel composition from the teeth;
(6) minimize damage to gums or mucous membranes in the mouth;
(7) can be worn comfortably and unobtrusively;
(8) are easily removed from the teeth, and leave no residue;
(9) are amenable to extended duration of wear or action; and
(10) sustained and controlled release of the whitening agent.

DETAILED DESCRIPTION OF THE INVENTION

I. Definitions and Nomenclature

Before describing the present invention in detail, it is to be understood that unless otherwise indicated this invention is not limited to specific hydrogel materials or manufacturing processes, as such may vary. It is also to be understood that the terminology used herein is for the purpose of describing particular embodiments only, and is not intended to be limiting. It must be noted that, as used in this specification and the appended claims, the singular forms "a," "an," and "the" include plural referents unless the context clearly dictates otherwise. Thus, for example, reference to "a hydrophilic polymer" includes not only a single hydrophilic polymer but also a combination or mixture of two or more different hydrophilic polymers, reference to "a plasticizer" includes a combination of mixture of two or more different plasticizers as well as a single plasticizer, and the like.

In describing and claiming the present invention, the following terminology will be used in accordance with the definitions set out below.

The definitions of "hydrophobic" and "hydrophilic" polymers are based on the amount of water vapor absorbed by polymers at 100% relative humidity. According to this classification, hydrophobic polymers absorb only up to 1 wt % water at 100% relative humidity ("rh"), while moderately hydrophilic polymers absorb 1-10% wt % water, hydrophilic polymers are capable of absorbing more than 10 wt % of water, and hygroscopic polymers absorb more than 20 wt % of water. A "water-swellable" polymer is one that absorbs an amount of water greater than at least 25 wt % of its own weight, and preferably at least 50 wt % of its own weight, upon immersion in an aqueous medium.

The term "crosslinked" herein refers to a composition containing intramolecular and/or intermolecular crosslinks, whether arising through covalent or noncovalent bonding. "Noncovalent" bonding includes both hydrogen bonding and electrostatic (ionic) bonding.

The term "polymer" includes linear and branched polymer structures, and also encompasses crosslinked polymers as well as copolymers (which may or may not be crosslinked), thus including block copolymers, alternating copolymers, random copolymers, and the like. Those compounds referred to herein as "oligomers" are polymers having a molecular weight below about 1000 Da, preferably below about 800 Da.

The term "hydrogel" is used in the conventional sense to refer to water-swellable polymeric matrices that can absorb a substantial amount of water to form elastic gels, wherein "matrices" are three-dimensional networks of macromolecules held together by covalent or noncovalent crosslinks. Upon placement in an aqueous environment, dry hydrogels swell to the extent allowed by the degree of cross-linking.

The term "tooth whitening composition" refers to a composition that contains a hydrogel, as defined herein, and a whitening agent.

The term "whitening agent" typically refers to an oxidizing agent such as a peroxide or a chlorite, as will be discussed in greater detail below. In some instances, the whitening agent may be an enzyme or other catalytic means for removing a stain from the teeth. The whitening agent may include one or more additional whitening agents, surfactants, antiplaque agents, antitartar agents and abrasive agents. The whitening agent may have additional therapeutic benefits.

The terms "tack" and "tacky" are qualitative. However, the terms "substantially nontacky" "slightly tacky" and "tacky," as used herein, may be quantified using the values obtained in a PKI or TRBT tack determination method, as follows. By "substantially nontacky" is meant a hydrogel composition that has a tack value that is less than about 25 g-cm/sec, by "slightly tacky" is meant a hydrogel composition that has a tack value in the range of about 25 g-cm/sec to about 100 g-cm/sec, and by "tack" is meant a hydrogel composition that has a tack value of at least 100 g-cm/sec.

The term "water-insoluble" refers to a compound or composition whose solubility in water is less than 5 wt %, preferably less than 3 wt %, more preferably less than 1 wt % (measured in water at 20° C.).

The term "translucent" is used herein to signify a material capable of transmitting light so that objects or images can be seen through the material. Translucent materials herein may or may not be "transparent," meaning that the material is optically clear. The term "translucent" indicates that a material is not "opaque," in which case objects and images cannot be seen through the material.

II. Compositions

The composition of the invention is comprised of a water-swellable, water-insoluble polymer, a blend of a hydrophilic polymer and a complementary oligomer capable of hydrogen bonding to the hydrophilic polymer, and a whitening agent. The water-swellable, water-insoluble polymer, i.e., a polymer that is capable of swelling when immersed in an aqueous liquid but that is insoluble in water within a selected pH range (generally less than pH 5.5), is a cellulose ester, or an acrylate-based polymer or copolymer, i.e., an acrylic acid or acrylic acid ester polymer or copolymer (an "acrylate" polymer). the polymer generally swells by at least 25 wt %, and preferably by at least 50 wt % of its own weight when immersed in water or aqueous solution. In some embodiments utilizing certain hydrophilic polymers, the composition may swell by as much as 1400 wt % of its dry weight.

The composition is preferably a tooth whitening composition, where the whitening agent functions to whiten the tooth surface to which the composition is applied. However, the whitening agent may have other utilities, for example as a therapeutic agent or other type of cosmeceutical agent, e.g., skin lightening). Therefore, the compositions described herein may find utility as pharmaceutical compositions to be applied to a body surface (e.g., teeth, nails, skin, mucosa, etc.) for the treatment of a disease state. For example, hydrogen peroxide also has antibiotic and anti-acne properties, as well as being a whitening agent. Therefore, the invention also contemplates treating an infection or acne by applying a hydrogen peroxide-containing composition of the invention to a body surface. Other diseases states include, by way of illustration and not limitation, fungal infections, acne, wounds, skin lightening, and so forth.

The hydrophilic polymer is generally a relatively high molecular weight polymer, and the complementary oligomer is generally a lower molecular weight polymer. For solid compositions, the water-swellable, water-insoluble polymer represents about 1-20 wt %, preferably about 6-12 wt % of the composition; the hydrophilic polymer represents about 20-80 wt %, preferably about 40-60 wt % of the composition; the complementary oligomer represents about 10-50 wt %, preferably about 15-35 wt % of the composition; and the whitening agent represents about 0.1-60 wt %, preferably about 1-30 wt % of the composition. Optimally, the complementary oligomer represents about 10-80 wt %, preferably about 20-50 wt % of the hydrophilic polymer/complementary oligomer blend.

In some instances, the complementary oligomer may also serve as a low molecular weight plasticizer. Alternatively, a different compound can be incorporated as an additional low molecular weight plasticizer and, if included, would be present as approximately 30 to 35 wt % of the composition.

For non-solid compositions, the water-swellable, water-insoluble polymer represents about 0.1-20 wt %, preferably about 2-6 wt % of the composition; the hydrophilic polymer represents about 1-20 wt %, preferably about 4-10 wt % of the composition; the complementary oligomer represents about 0.1-20 wt %, preferably about 0.5-10 wt % of the composition; and the whitening agent represents about 0.1-60 wt %, preferably about 1-40 wt % of the composition. Optimally, the complementary oligomer represents about 1-85 wt %, preferably about 5-50 wt % of the hydrophilic polymer/complementary oligomer blend.

The adhesion profile can be tailored based on type of polymer, the composition ratio and the extent of water in the blend. The water-swellable, water-insoluble polymer is selected so as to provide the desired adhesion profile with respect to hydration. That is, when the water-swellable, water-insoluble polymer is a cellulose ester, the composition is generally tacky prior to contact with water (e.g., with a moist surface) but gradually loses tack as the composition absorbs moisture. When the water-swellable, water-insoluble polymer is an acrylate polymer or copolymer, a composition is provided that is generally substantially nontacky prior to contact with water, but becomes tacky upon contact with a moist surface.

The water-swellable, water-insoluble polymer is capable of at least some degree of swelling when immersed in an aqueous liquid but is insoluble in water. The polymer may be comprised of a cellulose ester, for example, cellulose acetate, cellulose acetate propionate (CAP), cellulose acetate butyrate (CAB), cellulose propionate (CP), cellulose butyrate (CB), cellulose propionate butyrate (CPB), cellulose diacetate (CDA), cellulose triacetate (CTA), or the like. These cellulose esters are described in U.S. Pat. Nos. 1,698,049, 1,683,347, 1,880,808, 1,880,560, 1,984,147, 2,129,052, and 3,617,201, and may be prepared using techniques known in the art or obtained commercially. Commercially available cellulose esters suitable herein include CA 320, CA 398, CAB 381, CAB 551, CAB 553, CAP 482, CAP 504, all available from Eastman Chemical Company, Kingsport, Tenn. Such cellulose esters typically have a number average molecular weight of between about 10,000 and about 75,000.

Generally, the cellulose ester comprises a mixture of cellulose and cellulose ester monomer units; for example, commercially available cellulose acetate butyrate contains cellulose acetate monomer units as well as cellulose butyrate monomer units and unesterified cellulose monomer units, while cellulose acetate proprionate contains monomer units such as cellulose proprionate. Preferred cellulose esters herein are cellulose acetate propionate compositions and cellulose acetate butyrate compositions having the butyryl, propionyl, acetyl, and unesterified (OH) cellulose content as indicated below:

|  |  | Acetyl (%) | OH (%) | MW (g/mole) | $T_g$ (° C.) | $T_m$ (° C.) |
| --- | --- | --- | --- | --- | --- | --- |
| Cellulose Acetate Butyrate | 17-52% Butyrate | 2.0-29.5 | 1.1-4.8 | 12,000-70,000 | 96-141 | 130-240 |
| Cellulose Acetate Propionate | 42.5-47.7% Propionate | 0.6-1.5 | 1.7-5.0 | 15,000-75,000 | 142-159 | 188-210 |

The preferred molecular weight, glass transition temperature ($T_g$) and melting temperature ($T_m$) are also indicated. Also, suitable cellulosic polymers typically have an inherent viscosity (I.V.) of about 0.2 to about 3.0 deciliters/gram, preferably about 1 to about 1.6 deciliters/gram, as measured at a temperature of 25° C. for a 0.5 gram sample in 100 ml of a 60/40 by weight solution of phenol/tetrachloroethane. When prepared using a solvent casting technique, the water-swellable, water-insoluble polymer should be selected to provide greater cohesive strength and thus facilitate film forming (generally, for example, cellulose acetate propionate tends to improve cohesive strength to a greater degree than cellulose acetate butyrate).

Other preferred water-swellable polymers are acrylate polymers, generally formed from acrylic acid, methacrylic acid, methyl acrylate, ethyl acrylate, methyl methacrylate, ethyl methacrylate, and/or other vinyl monomers. Suitable acrylate polymers are those copolymers available under the tradename "Eudragit" from Rohm Pharma (Germany). The Eudragit series E, L, S, RL, RS and NE copolymers are available solubilized in organic solvent, in an aqueous dispersion, or as a dry powder. Preferred acrylate polymers are copolymers of methacrylic acid and methyl methacrylate, such as the Eudragit L and Eudragit S series polymers. Particularly preferred such copolymers are Eudragit L-30D-55 and Eudragit L-100-55 (the latter copolymer is a spray-dried form of Eudragit L-30D-55 that can be reconstituted with water). The molecular weight of the Eudragit L-3-D-55 and Eudragit L-100-55 copolymer is approximately 135,000 Da, with a ratio of free carboxyl groups to ester groups of approximately 1:1. The copolymer is generally insoluble in aqueous fluids having a pH below 5.5. Another particularly suitable methacrylic acid-methyl methacrylate copolymer is Eudragit S-100, which differs from Eudragit L-30D-55 in that the ratio of free carboxyl groups to ester groups is approximately 1:2. Eudragit S-100 is insoluble at pH below 5.5, but unlike Eudragit L-30D-55, is poorly soluble in aqueous fluids having a pH in the range of 5.5 to 7.0. This copolymer is soluble at pH 7.0 and above. Eudragit L-100 may also be used, which has a pH-dependent solubility profile between that of Eudragit L-30D-55 and Eudragit S-100, insofar as it is insoluble at a pH below 6.0. It will be appreciated by those skilled in the art that Eudragit L-3-D-55, L-100-55, L-100, and S-100 can be replaced with other acceptable polymers having similar pH-dependent solubility characteristics. Other suitable acrylate polymers are those methacrylic acid/ethyl acrylate copolymers available under the tradename "Kollicoat" from BASF AG (Germany). For example, Kollicoat MAE has the same molecular structure as Eudragit L-100-55.

When the water-swellable polymer is an acrylic acid or acrylate polymer, a hydrogel is provided that can be reversibly dried, i.e., after removal of water and any other solvents, the dried hydrogel may be reconstituted to its original state by addition of water. In addition, hydrophilic hydrogels prepared with an acrylic acid/acrylate water-swellable polymer are generally substantially nontacky prior to contact with water, but become tacky upon contact with a moist surface, such as is found in the interior of the mouth, such as on the surface of the teeth. This property of being nontacky prior to contact with water enables positioning or repositioning on a chosen surface before, or as the hydrogel becomes tacky. Once hydrated, the hydrogel becomes tacky and adheres to the surface of the teeth.

In addition, acrylate-containing compositions can generally provide swelling in the range of about 400% to 1500% upon immersion of the hydrogel composition in water or other aqueous liquid, at a pH of less than 5.5, although the ratio of the acrylate polymer to the hydrophilic polymer/complementary oligomer blend can be selected such that the rate and extent of the swelling in an aqueous environment has a predetermined pH-dependence. This feature also provides for retroactive incorporation of whitening agents or other agents, such as loading the composition with peroxide, peroxy acids, chlorites, stabilizers, flavoring agents, etc.

By contrast, incorporating a cellulose ester as the water-swellable polymer renders the hydrogel tacky prior to application to a moist surface, but nontacky upon absorption of water. It will be appreciated that such a composition may be desirable when a decrease in tack is desired for ultimate removal of the product from the teeth.

The second component of the hydrogel composition is a blend of a hydrophilic polymer and a complementary oligomer capable of hydrogen bonding to the hydrophilic polymer, and optionally capable of ionically or covalently bonding to the hydrophilic polymer as well. Suitable hydrophilic polymers include repeating units derived from an N-vinyl lactam monomer, a carboxy vinyl monomer, a vinyl ester monomer, an ester of a carboxy vinyl monomer, a vinyl amide monomer, and/or a hydroxy vinyl monomer. Such polymers include, by way of example, poly(N-vinyl lactams), poly(N-vinyl acrylamides), poly(N-alkylacrylamides), substituted and unsubstituted acrylic and methacrylic acid polymers (e.g., polyacrylic acids and polymethacrylic acids), polyvinyl alcohol (PVA), polyvinylamine, copolymers thereof and copolymers with other types of hydrophilic monomers (e.g. vinyl acetate).

Poly(N-vinyl lactams) useful herein are preferably non-crosslinked homopolymers or copolymers of N-vinyl lactam monomer units, with N-vinyl lactam monomer units representing the majority of the total monomeric units of a poly(N-vinyl lactams) copolymer. Preferred poly(N-vinyl lactams) for use in conjunction with the invention are prepared by polymerization of one or more of the following N-vinyl lactam monomers: N-vinyl-2-pyrrolidone; N-vinyl-2-valerolactam; and N-vinyl-2-caprolactam. Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

Poly (N-alkylacrylamides) include, by way of example, poly(methacrylamide) and poly(N-isopropyl acrylamide)(P-NIPAM).

Polymers of carboxy vinyl monomers are typically formed from acrylic acid, methacrylic acid, crotonic acid, isocrotonic acid, itaconic acid and anhydride, a 1,2-dicarboxylic acid such as maleic acid or fumaric acid, maleic anhydride, or mixtures thereof, with preferred hydrophilic polymers within this class including polyacrylic acid and polymethacrylic acid, with polyacrylic acid most preferred.

Preferred hydrophilic polymers herein are the following: poly(N-vinyl lactams), particularly polyvinyl pyrrolidone (PVP) and polyvinyl caprolactam (PVCap); poly(N-vinyl acetamides), particularly polyacetamide per se; polymers of carboxy vinyl monomers, particularly polyacrylic acid and polymethacrylic acid; and copolymers and blends thereof. PVP and PVCap are particularly preferred.

The molecular weight of the hydrophilic polymer is not critical; however, the number average molecular weight of the hydrophilic polymer is generally in the range of approximately 100,000 to 2,000,000, more typically in the range of approximately 500,000 to 1,500,000. The oligomer is "complementary" to the hydrophilic polymers in that it is capable of hydrogen bonding thereto. Preferably, the complementary oligomer is terminated with hydroxyl groups, amino or carboxyl groups. The oligomer typically has a glass transition Temperature $T_g$ in the range of about −100° C. to about −30° C. and a melting temperature $T_m$ lower than about 20° C. The oligomer may be also amorphous. The difference between the $T_g$ values of the hydrophilic polymer and the oligomer is preferably greater than about 50° C., more preferably greater than about 100° C., and most preferably in the range of about 150° C. to about 300° C. The hydrophilic polymer and complementary oligomer should be compatible, i.e. capable of forming a homogeneous blend that exhibits a single $T_g$, intermediate between those of the unblended components.

Generally, the complementary oligomer will have a molecular weight in the range from about 45 to about 800, preferably in the range of about 45 to about 600. The complementary oligomer is preferably a low molecular weight polyalkylene glycol (molecular weight 300-600) such as polyethylene glycol 400, which can also serve as a low molecular weight plasticizer. Alternatively, a different compound can be incorporated as an additional low molecular weight plasticizer, in which case any of the low molecular weight plasticizers described below can be used. In one embodiment of the invention, the complementary oligomer is a complementary low molecular weight or oligomeric plasticizer that contains at least two functional groups per molecule that are capable of hydrogen bonding to the hydrophilic polymer.

Examples of suitable complementary oligomers include, but are not limited to, low molecular weight polyalcohols (e.g. glycerol), monomeric and oligoalkylene glycols such as ethylene glycol and propylene glycol, ether alcohols (e.g., glycol ethers), carbonic diacids, alkane diols from butane diol to octane diol, including carboxyl-terminated and amino-terminated, derivatives of polyalkylene glycols. Polyalkylene glycols, optionally carboxyl-terminated, are preferred herein, and polyethylene glycol having a molecular weight in the range of about 300 to 600 is an optimal complementary oligomer.

It will be appreciated from the foregoing that a single compound, e.g., a low molecular weight polyalkylene glycol such as polyethylene glycol having a molecular weight in the range of about 300 to 600, can serve as both the complementary oligomer and the low molecular weight plasticizer.

As discussed in U.S. Patent Publication No. 2002/0037977 for "Preparation of Hydrophilic Pressure Sensitive Adhesives Having Optimized Adhesive Properties", the ratio of the hydrophilic polymer to the complementary oligomer in the aforementioned blend affects both adhesive strength and the cohesive strength. As explained in the aforementioned patent application, the complementary oligomer decreases the glass transition of the hydrophilic polymer/complementary oligomer blend to a greater degree than predicted by the Fox equation, which is given by equation (1)

$$\frac{1}{T_{g\ predicted}} = \frac{w_{pol}}{T_{g_{pol}}} + \frac{w_{pl}}{T_{g_{pl}}} \qquad (1)$$

where $T_{g\ predicted}$ is the predicted glass transition temperature of the hydrophilic polymer/complementary oligomer blend, $w_{pol}$ is the weight fraction of the hydrophilic polymer in the blend, $w_{pl}$ is the weight fraction of the complementary oligomer in the blend, $T_{g\ pol}$ is the glass transition temperature of the hydrophilic polymer, and $T_{g\ pl}$ is the glass transition temperature of the complementary oligomer. As also explained in that patent application, an adhesive composition having optimized adhesive and cohesive strength can be prepared from a hydrophilic polymer and a complementary oligomer by selecting the components and their relative amounts to give a predetermined deviation from $T_{g\ predicted}$. Generally, to maximize adhesion, the predetermined deviation from $T_{g\ predicted}$ will be the maximum negative deviation, while to minimize adhesion, any negative deviation from $T_{g\ predicted}$ is minimized.

As the complementary oligomer may itself act as a plasticizer, it is not generally necessary to incorporate an added plasticizer. However, inclusion of an additional low molecular weight plasticizer in the composition is optional and may, in some cases, be advantageous. Suitable low molecular weight plasticizers include: dialkyl phthalates, dicycloalkyl phthalates, diaryl phthalates, and mixed alkylaryl phthalates, as represented by dimethyl phthalate, diethyl phthalate, dipropyl phthalate, di(2-ethylhexyl)-phthalate, di-isopropyl phthalate, diamyl phthalate and dicapryl phthalate; alkyl and aryl phosphates such as tributyl phosphate, trioctyl phosphate, tricresyl phosphate, and triphenyl phosphate; alkyl citrate and citrate esters such as trimethyl citrate, triethyl citrate, tributyl citrate, acetyl triethyl citrate, and trihexyl citrate; dialkyl adipates such as dioctyl adipate (DOA); also referred to as bis(2-ethylhexyl)adipate), diethyl adipate, di(2-methylethyl)adipate, and dihexyl adipate; dialkyl tartrates such as diethyl tartrate and dibutyl tartrate; dialkyl sebacates such as diethyl sebacate, dipropyl sebacate and dinonyl sebacate; dialkyl succinates such as diethyl succinate and dibutyl succinate; alkyl glycolates, alkyl glycerolates, glycol esters and glycerol esters such as glycerol diacetate, glycerol triacetate (triacetin), glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate; and mixtures thereof. Preferred low molecular weight plasticizers for the continuous hydrophilic phase are triethyl citrate, diethyl phthalate, and dioctyl adipate, with dioctyl adipate most preferred.

The properties of the composition of the invention are readily controlled by adjusting one or more parameters during fabrication. For example, the adhesive strength of the composition can be controlled during manufacture in order to increase, decrease, or eliminate adhesion. This can be accomplished by varying type and/or amount of different components, or by changing the mode of manufacture. Also, with respect to the fabrication process, compositions prepared using a conventional melt extrusion process are generally, although not necessarily, somewhat less tacky than compositions prepared using a solution cast technique. Furthermore, the degree to which the hydrogel composition will swell upon contact with water can be varied by selecting different water-swellable polymers, and, in those compositions containing a continuous hydrophilic phase, by adjusting the ratio of the water-swellable, water-insoluble polymer to the hydrophilic polymer/complementary plasticizer blend. These compositions may vary in appearance from clear, transparent to translucent to opaque. In addition, certain compositions may be rendered translucent by changing the relative quantities of the components in the hydrophilic phase (e.g., by decreasing the amount of the cellulose ester), or by changing the fabrication method (translucent hydrogels are more readily obtained using solution casting than melt extrusion). In this manner, the translucent composition allows the user to observe the whitening process while it is occurring and determine when the teeth have been sufficiently whitened.

The above-described hydrogel compositions contain a whitening agent and thereby act as a delivery system when applied to the teeth. The release of whitening agents "loaded" into the present hydrogel compositions typically involves both absorption of water and desorption of the agent via a swelling-controlled diffusion mechanism. Whitening agent-containing hydrogel compositions may be employed in a manner similar to that of topical pharmaceutical formulations, for example.

Suitable tooth whitening agents include peroxides, metal chlorites, perborates, percarbonates, peroxyacids, and combinations thereof. Suitable peroxide compounds include hydrogen peroxide, calcium peroxide, carbamide peroxide, and mixtures thereof. The preferred peroxides are hydrogen and carbamide peroxide. Other suitable peroxides include organic peroxides, including but not limited to dialkyl peroxides such as t-butyl peroxide and 2,2 bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. The whitening agent is preferably a peroxide, such as hydrogen peroxide or carbamide peroxide, and most preferably is hydrogen peroxide.

Suitable metal chlorites include calcium chlorite, barium chlorite, magnesium chlorite, lithium chlorite, sodium chlorite, and potassium chlorite; hypochlorite and chlorine dioxide. The preferred chlorite is sodium chlorite.

III. Optional Additives

The composition can also include any pharmaceutically active agent useful in treating physiological conditions involving the teeth and surrounding tissue. As used herein, a "pharmaceutically active agent" is any substance that can be released from the composition to treat an undesirable physiological condition. Undesirable, physiological conditions involving the teeth or surrounding tissue which are amenable to treatment with the present device include: halitosis; periodontal and oral infections; periodontal lesions; dental caries or decay; gingivitis; and other periodontal diseases.

The pharmaceutically active agent can be, for example, an non-steroidal anti-inflammatory/analgesic; steroidal anti-inflammatory agents; local anesthetics; bactericides/disinfectants; antibiotics; antifungals; tooth desensitizing agents; fluoride anticavity/antidecay agents; anti-tartar/anti-calculus agents; enzymes which inhibit the formation of plaque, calculus or dental caries; abrasive agents such as pyrophosphates; metal chelators such as ethylenediaminetetraacetic acid, tetrasodium salt; anti-oxidants such as butylated hydroxyanisole; butylated hydroxy toluene; nutritional supplements for local delivery to the teeth and surrounding tissue; and so forth.

Suitable non-steroidal anti-inflammatory/analgesic agents include acetaminophen; methyl salicylate; monoglycol salicylate; aspirin; mefenamic acid; flufenamic acid; indomethacin; diclofenac; alclofenac; diclofenac sodium; ibuprofen; flurbiprofen; fentizac; bufexamac; piroxicam; phenylbutazone; oxyphenbutazone; clofezone; pentazocine; mepirizole; and tiaramide hydrochloride.

Suitable steroidal anti-inflammatory agents include hydrocortisone; prednisolone; dexamethasone; triamcinolone acetonide; fluocinolone acetonide; hydrocortisone acetate; prednisolone acetate; methylprednisolone; dexamethasone acetate; betamethasone; betamethasone valerate; flumetasone; flourometholone; budesonide; and beclomethasone dipropionate.

Suitable local anesthetics include dibucaine hydrochloride; dibucaine; lidocaine hydrochloride; lidocaine; benzocaine; p-buthylaminobenzoic acid 2-(diethylamino) ethyl ester hydrochloride; procaine hydrochloride; tetracaine hydrochloride; chloroprocaine hydrochloride; oxyprocaine hydrochloride; mepivacaine; cocaine hydrochloride; and piperocaine hydrochloride.

Suitable bactericides/disinfectants include thimerosol; phenol; thymol; benzalkonium chloride; benzethonium chloride; chlorhexidine; providone iodide; cetylpyridinium chloride; eugenol, and trimethylammonium bromide.

Suitable antibiotics include penicillin; meticillin; oxacillin; cefalotin; cefaloridin; erythromycin; lincomycin; tetracycline; chlortetracycline; oxytetracycline; metacycline; chloramphenicol; kanamycin; streptomycin; gentamicin; bacitracin; and cycloserine. Suitable antifungal drugs include amphotericin; clotrimazole; econazole nitrate; fluconazole; griseofulvin; itraconazole; ketoconazole; miconazole; nystatin; terbinafine hydrochloride; undecenoic acid; and zinc undecenoate.

Suitable tooth-desensitizing agents include potassium nitrate and strontium chloride. Suitable fluoride anticavity/antidecay agents include sodium fluoride, potassium fluoride and ammonium fluoride.

Additional whitening agents include anti-tartar/anti-calculus agents, including phosphates such as pyrophosphates, polyphosphates, polyphosphonates (e.g., ethane-1-hydroxy-1,1-diphosphonate, 1-azacycloheptane-1,1-diphosphonate, and linear alkyl diphosphonates), and salts thereof; linear carboxylic acids; and sodium zinc citrate; and mixtures thereof. Preferred pyrophosphate salts are the dialkali metal pyrophosphate salts, tetra-alkali metal pyrophosphate salts; and the hydrated or unhydrated forms of disodium dihydrogen pyrophosphate ($Na_2H_2P_2O_7$), tetrasodium pyrophosphate ($Na_4P_2O_7$), and tetrapotassium pyrophosphate ($K_4P_2O_7$). The pyrophosphate salts are described in more detail in Kirk & Othmer, Encyclopedia of Clinical Technology Third Edition, Volume 17, Wiley-Interscience Publishers (1982), the entire disclosure of which is herein incorporated by reference in its entirety. Optionally, whitening agents can also include tartar dissolving agents such as betaines, amine oxides and quaternaries, as described in U.S. Pat. No. 6,315,991 to Zofchak.

Enzymatic agents that would act to inhibit the formation of plaque, calculus or dental caries would also be useful in the compositions. The enzymatic agents can be stored together with the whitening agent, or they can be positioned in a different layer within a multiple layer system as described herein. Suitable enzymes include: proteases that break down salivary proteins which are absorbed onto the tooth surface and form the pellicle, or first layer of plaque; lipases which destroy bacteria by lysing proteins and lipids which form the structural component of bacterial cell walls and membranes; dextranases, glucanohydrolases, endoglycosidases, and mucinases which break down the bacterial skeletal structure which forms a matrix for bacterial adhesion to the tooth; and amylases which prevent the development of calculus by breaking-up the carbohydrate-protein complex that binds calcium. Preferred enzymes include any of the commercially available proteases; dextranses; glucanohydrolases; endoglycosidases; amylases; mutanases; lipases; mucinases; and compatible mixtures thereof. In some embodiments, an enzymatic whitening agent may be utilized.

Optionally, an enzymatic whitening agent is a peroxidase such that peroxide is generated in situ. When an enzymatic whitening or antiplaque agent is incorporated into the composition, the composition should be such that the enzyme is maintained in its active form, e.g., the pH should be approximately neutral, and peroxide may be omitted or contained in a separate layer.

Suitable nutritional supplements for local delivery to the teeth and surrounding tissue include vitamins (e.g., vitamins C and D, thiamine, riboflavin, calcium pantothenate, niacin, folic acid, nicotinamide, pyridoxine, cyanocobalamin, para-aminobenzoic acid, and bioflavonoids); and minerals (e.g., calcium, phosphorus, fluoride, zinc, manganese, and potassium); and mixtures thereof. Vitamins and minerals useful in the present invention are disclosed in *Drug Facts and Comparisons* (loose leaf drug information service), Wolters Kluer Company, St. Louis, Mo. 1997, pp 3.17; the entire disclosure of which is herein incorporated by reference.

The composition can also include any cosmetically active agent. As used herein, a "cosmetically active agent" includes any substance that can be released from the composition to effect a desired change in the appearance of the teeth or surrounding tissue, or which imparts a socially desirable characteristic to the user, such as fresh breath. For example, a cosmetically active agent can be a breath freshener or an agent which effects whitening or bleaching of the teeth. Recognizing that in some cultures or in certain segments of Western society coloration of the teeth may be significant or desirable, the cosmetically active agent can also be any agent which imparts a color or tint to the teeth.

Additional whitening agents may be included in the composition. For example, surfactants such as detergents, may also be present, and will work together with the whitening agents described above to provide a brighter appearance to the teeth.

In any of these embodiments, a tooth whitening composition of the invention preferably includes a peroxide for whitening the teeth, and may also include conventional additives such as fillers, preservatives, pH regulators, softeners, thickeners, colorants, pigments, dyes, refractive particles, stabilizers, toughening agents, pharmaceutical agents, flavoring or breath freshening agents, and permeation enhancers. In those embodiments wherein adhesion is to be reduced or eliminated, conventional detackifying agents may also be used. These additives, and amounts thereof, are selected in such a way that they do not significantly interfere with the desired chemical and physical properties of the tooth whitening composition, or interfere with the delivery of the tooth whitening agent can be included in the composition. Such additional ingredients include coloring compounds; food additives; flavorants; sweeteners; and preservatives.

Any natural of synthetic flavorant or food additive, such as those described in Chemicals Used in Food Processing, Pub. No. 1274, National Academy of Sciences, pages 63-258 (the entire disclosure of which is herein incorporated by reference) can be used. Suitable flavorants include wintergreen, peppermint, spearmint, menthol, fruit flavors, vanilla, cinnamon, spices, flavor oils and oleoresins, as known in the art, as well as combinations thereof. The amount of flavorant employed is normally a matter of preference, subject to such factors as flavor type, individual flavor, and strength desired. Preferably, the composition comprises from about 0.1 wt % to about 5 wt % flavorant.

Sweeteners useful in the present invention include sucrose, fructose, aspartame, xylitol and saccharine. Preferably, the composition comprises sweeteners in an amount from about 0.001 wt % to about 5.0 wt %.

The suitable substrate can be translucent so that the composition is unobtrusive when worn. However, the substrate or the composition can optionally be colored, so that the composition is obtrusive when worn. Preferably, if coloring is desired, the color will be present in the substrate. For example, the substrate can be colored with bright or vibrant colors which a consumer may find pleasing. The substrate can therefore comprise a colorizing compound, such as, for example, a dye, pigment or substance that can impart color when added to the material forming the substrate.

For example, colorizing compounds of the type commonly used with a food, drugs, or cosmetics in connection with the human body, especially color additives permitted for use in foods which are classified as "certifiable" or "exempt from certification," can be used to color the substrate. The colorizing compounds used to color the substrate can be derived from natural sources such as vegetables, minerals or animals, or can be man-made counterparts of natural derivatives.

Colorizing compounds presently certified under the Food Drug & Cosmetic Act for use in food and ingested drugs include dyes such as FD&C Red No. 3 (sodium salt of tetraiodofluorescein); Food Red 17 (disodium salt of 6-hydroxy-5-{(2-methoxy-5-methyl-4-sulphophenyl)azo}-2-naphthalenesulfonic acid); Food Yellow 13 (sodium salt of a mixture of the mono and disulfonic acids of quinophthalone or 2-(2-quinolyl)indanedione); FD&C Yellow No. 5 (sodium salt of 4-p-sulfophenylazo-1-p-sulfophenyl-5-hydroxypyrazole-3 carboxylic acid); FD&C Yellow No. 6 (sodium salt of p-sulfophenylazo-B-napthol-6-monosulfonate); FD&C Green No. 3 (disodium salt of 4-{[4-(N-ethyl-p-sulfobenzylamino)-phenyl]-(4-hydroxy-2-sulfonium-phenyl)-m ethylene}-[1-(N-ethyl-N-p-sulfobenzyl)-3, 5-cyclohexadienimine]); FD&C Blue No. 1 (disodium salt of dibenzyldiethyl-diaminotriphenylcarbinol trisulfonic acid anhydrite); FD&C Blue No. 2 (sodium salt of disulfonic acid of indigotin); FD&C Red No. 40; Orange B; and Citrus Red No. 2; and combinations thereof in various proportions.

Colorization compounds exempt from FDA certification include annatto extract; beta-apo-8'-carotenal; beta-carotene; beet powder; canthaxanthin; caramel color; carrot oil; cochineal extract (carmine); toasted, partially defatted, cooked cottonseed flour, ferrous gluconate; fruit juice; grape color extract; grape skin extract (enocianina); paprika; paprika oleoresin; riboflavin; saffron; turmeric; turmeric oleoresin; vegetable juice; and combinations thereof in various proportions.

The form of the colorizing compound for use in the composition preferably includes dye form additives, but may also include lake forms which are compatible with the material comprising the substrate. Water soluble dyes, provided in the form of powders, granules, liquids or other special-purpose forms, can be used in accordance with the present method. Preferably, the "lake", or water insoluble form of the dye, is used for coloring the substrate. For example, if a suspension of a colorizing compound is to be used, a lake form additive can be employed. Suitable water insoluble dye lakes prepared by extending calcium or aluminum salts of FD&C dyes on alumina include FD&C Green #1 lake, FD&C Blue #2 lake, FD&C R&D #30 lake and FD&C # Yellow 15 lake.

Other suitable colorizing compounds include non-toxic, water insoluble inorganic pigments such as titanium dioxide; chromium oxide greens; ultramarine blues and pinks; and ferric oxides. Such pigments preferably have a particle size in the range of about 5 to about 1000 microns, more preferably about 250 to about 500 microns.

The concentration of the colorizing compound in the substrate is preferably from about 0.05 wt % to about 10 wt %, and is more preferably from about 0.1 wt % to about 5 wt %.

More than one colorizing compound can be present in the substrate, so that multiple colors are imparted therein. These multiple colors can be patterned into stripes, dots, swirls, or any other design which a consumer may find pleasing. The colorizing compound can also be used with other appearance-enhancing substances such as glitter particles.

Absorbent fillers may be advantageously incorporated to control the degree of hydration when the adhesive is on the tooth surface. Such fillers can include microcrystalline cellulose, talc, lactose, kaolin, mannitol, colloidal silica, alumina, zinc oxide, titanium oxide, magnesium silicate, magnesium aluminum silicate, hydrophobic starch, calcium sulfate, calcium stearate, calcium phosphate, calcium phosphate dihydrate, clays such as laponite, woven and non-woven paper and cotton materials. Other suitable fillers are inert, i.e., substantially non-adsorbent, and include, for example, polyethylenes, polypropylenes, polyurethane polyether amide copolymers, polyesters and polyester copolymers, nylon and rayon. A preferred filler is colloidal silica, e.g., Ca-O-Sil® (Cabot Corporation, Boston Mass).

Preservatives include, by way of example, p-chloro-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, and propylene glycol.

Compounds useful as pH regulators include, but are not limited to, glycerol buffers, citrate buffers, borate buffers, phosphate buffers, or citric acid-phosphate buffers may also be included so as to ensure that the pH of the hydrogel composition is compatible with that of the environment of the mouth and will not leach minerals from the surface of the teeth. In order to optimize whitening without demineralization of the teeth, calcium and/or fluoride salts can be included in the composition.

Suitable softeners include citric acid esters, such as triethylcitrate or acetyl triethylcitrate, tartaric acid esters such as dibutyltartrate, glycerol esters such as glycerol diacetate and glycerol triacetate; phthalic acid esters, such as dibutyl phthalate and diethyl phthalate; and/or hydrophilic surfactants, preferably hydrophilic non-ionic surfactants, such as, for example, partial fatty acid esters of sugars, polyethylene glycol fatty acid esters, polyethylene glycol fatty alcohol ethers, and polyethylene glycol sorbitan-fatty acid esters.

Preferred thickeners herein are naturally occurring compounds or derivatives thereof, and include, by way of example: collagen; galactomannans; starches; starch derivatives and hydrolysates; cellulose derivatives such as methyl cellulose, hydroxypropylcellulose, hydroxyethyl cellulose, and hydroxypropyl methyl cellulose; colloidal silicic acids; and sugars such as lactose, saccharose, fructose and glucose. Synthetic thickeners such as polyvinyl alcohol, vinylpyrrolidone-vinylacetate-copolymers, polyethylene glycols, and polypropylene glycols may also be used.

The substrate can also be embedded or decorated with decorative items such as beads, rhinestones, or the like, as long as these items do not interfere with the visco-elastic properties of the substrate required for proper deformation of the composition onto the teeth, as described above. The substrate can also display letters, words, or images designed to be pleasing or attractive to a consumer.

IV. Fabrication Processes

The compositions of the invention are generally melt extrudable, and thus may be prepared using a simple blending and extruding process. The components of the composition are weighed out and then admixed, for example using a Brabender or Baker Perkins Blender, generally although not necessarily at an elevated temperature, e.g., about 90 to 140° C. Solvents or water may be added if desired. The resulting composition can be extruded using a single or twin extruder, or pelletized. Alternatively, the components of the composition can be melted one at a time, and then mixed prior to extrusion. Preferably the composition is extruded directly onto a suitable substrate such as a backing layer or a releasable liner, and then pressed. The thickness of the resulting hydrogel-containing film, for most purposes, will be in the range of about 0.050 to 0.80 mm, more usually in the range of about 0.37 to 0.47 mm.

Alternatively, the compositions may be prepared by solution casting, by admixing the components of the composition in a suitable solvent, e.g., a volatile solvent such as ethyl acetate, or lower alkanols (e.g., ethanol, isopropyl alcohol, etc.) are particularly preferred, at a concentration typically in the range of about 35 to 60% w/v. The solution is cast onto a suitable substrate such as a backing layer or releasable liner, as above. Both admixture and casting are preferably carried out at ambient temperature. The substrate coated with the film is then baked at a temperature in the range of about 80 to 100° C., optimally about 90° C., for time period in the range of about one to four hours, optimally about two hours. Accordingly, one embodiment of the invention is a method for preparing a hydrogel film suitable for incorporation into a composition of the invention, which involves the following steps: preparing a solution of a water-swellable, water-insoluble polymer, a hydrophilic polymer, and a complementary oligomer capable of hydrogen bonding to the hydrophilic polymer, in a solvent; depositing a layer of the solution on a substrate to provide a coating thereon; and heating the coated substrate to a temperature in the range of about 80 to 100° C. for a time period in the range of about 1 to 4 hours, thereby providing a hydrogel film on the substrate.

When tacky hydrogel compositions are desired, melt extrusion is the preferred process, although solution casting may still be used. For preparation of substantially nontacky compositions, solution casting is preferred. Also, melt extrusion can be used for any of the compositions of the invention. Also, either melt extrusion or solution casting techniques can be used to prepare translucent compositions, although solution casting is typically preferred for these embodiments. Accordingly, another embodiment of the invention is a method of forming a composition comprised of a continuous hydrophilic phase, which involves the following steps: melt processing through an extruder a mixture of a water-swellable, water-insoluble polymer, a hydrophilic polymer, and a complementary oligomer capable of hydrogen bonding to the hydrophilic polymer, to form an extruded composition; extruding the composition as a film of desired thickness onto a suitable substrate; and, when cooled, and loading the film with an aqueous solution of a peroxide to obtain a concentration of whitening agent of from about 1 to 20 wt %.

The invention also contemplates having a multiple layer system that includes one or more additional hydrogel or non-hydrogel layers. For example, it may be desirable to include additional active agents that may not be compatible with the whitening agent during storage. In this manner, one layer can be a whitening agent-containing hydrogel layer and the other layer(s) can contain additional actives. These other layers can be made of the hydrogel composition described herein, or any other biocompatible formulation known in the art (e.g., polyisobutylene, dimethyl siloxane, ethylene vinyl acetate, polyvinylacetate, cellulose acetate, butyrate, propionate, ethyl cellulose and water insoluble acrylates). In addition, depending on ordering of the layers, it may be desired to have a tacky layer, e.g., the layer to be positioned directly on the teeth, and a non-tacky layer, e.g., the outer layer that is positioned nearest the lips. Another advantage of having multiple layer system is that the ratio of polymers used in the outermost layer can be varied to achieve a non-tacky layers to as to avoid having to include a separate backing layer in the product.

In one embodiment, the composition comprises: an outer substrate that serves as the external surface of the composition following application to the tooth surface; a tooth contact adhesive layer adhered thereto, which generally will be an adhesive composition of the invention, optionally containing additional whitening agents; and a removable release liner. Upon removal of a release liner, for example, the composition is applied to the surface of the teeth to be treated, and placed on the tooth surface so that the tooth-contacting layer is in contact. In another embodiment, the composition is packaged without a backing layer or a release liner. Accordingly, once removed from the packaging, the composition is ready to be applied to the tooth surface.

The substrate is the primary structural element and provides the composition with support, either during manufacture or during use. The material used for the substrate should be inert and incapable of absorbing the hydrogel composition. Also, the material used for the substrate should permit the device to follow the contours of the teeth and be worn comfortably in the mouth without rubbing or otherwise irritating the lips or tongue. Examples of materials useful for the substrate are polyesters, polyethylene, polypropylene, polyurethanes and polyether amides. The substrate is preferably in the range of about 15 microns to about 250 microns in thickness, and may, if desired, be pigmented, metallized, or provided with a matte finish suitable for writing.

In one embodiment, the substrate is preferably although not necessarily occlusive (i.e., not "breathable"), and does not allow the whitening agent in the composition to leak through the layer, and contact the mucous membranes of the mouth and gums. When ready for use, the composition is pre-moistened so that the tackiness is increased and the composition will adhere to the teeth. One advantage of this embodiment is that the whitening agent cannot substantially leak out through the substrate and cause irritation in those individuals sensitive to the whitening agent or to any unpleasant flavor or sensation.

Other suitable substrate materials can be non-polymeric materials such as waxes (e.g., microcrystalline or paraffin waxes) a or wax/foam laminate. Paraffin waxes are low molecular weight straight-chain hydrocarbons, with melting points of about 48-75° C. and molecular weights of about 300-1400 g/mol, and are typically made by the Fischer-Tropsch synthesis. Microcrystalline waxes are flexible and amorphous-like in appearance and tend to have a higher tensile strength and smaller crystal size than paraffin waxes. Microcrystalline waxes typically have melting points of about 60-95° C. and molecular weights of about 580-700 g/mol, and predominantly contain branched-chain hydrocarbons and some ring-type compounds, although straight-chain hydrocarbons can be present. The substrate material can also be an open-cell foam such as a polyurethane, polystyrene or polyethylene foam.

Alternatively, in another embodiment, the substrate is non-occlusive, and therefore can fully hydrate in situ, in position on the teeth.

The release liner is a disposable element that serves to protect the system prior to application. The release liner should be formed from a material impermeable to the whitening agent and hydrogel composition, and that is easily stripped from the contact adhesive. Release liners are typically treated with silicone or fluorocarbons, and are commonly made from polyesters and polyethylene terephthalate.

A preferred composition is typically prepared using an acrylate polymer as the water-insoluble, water-swellable polymer; and a blend of polyvinylpyrrolidone and polyethylene glycol as the blend of a hydrophilic polymer and a complementary oligomer capable of hydrogen bonding to the hydrophilic polymer.

An adhesive film of the composition can be manufactured by thermally melting and mixing the above components together at temperatures ranging from about 100 to 170° C. The film is extruded to a desired thickness on a suitable substrate. Alternatively, the components can be dissolved in a single or mixture of solvents, and the solution can be cast on a releasing or backing film. The solvents are then evaporated to obtain a hydrogel film.

One method of loading the composition with the whitening agent comprises layering a desired whitening agent in aqueous solution onto the surface of the hydrogel placed on a suitable substrate, or to place the whitening agent directly on the substrate. The release liner is then assembled on top of the composition, forming a sandwich structure, and the solution containing the whitening agent is absorbed into the composition due to its water-swellable properties. Alternatively, the composition layered onto the substrate can be submerged in a solution containing the desired concentration of whitening agent, and the solution absorbed into the composition. By measuring the rate of weight gain on absorbing the liquid, the percent loading of the composition with the whitening agent can be determined and controlled.

Another approach to loading the whitening agent into the composition is to add the whitening agent as a solid or as a solution to the composition dissolved in solvent. The mixture is then cast as usual on a suitable substrate and allowed to dry, although a lower drying temperature is desired when using this method of loading. Compositions prepared in this manner can be dried at ambient temperature for a time period ranging from about 1 hour to several days.

A typical film thickness is from about 0.050 to 0.80 mm, preferably 0.25 to 0.50 mm. The thickness of the film is not critical, and can be varied according to the concentration of whitening agent incorporated into the film, the length of time the film is to be exposed to the teeth, the level of comfort desired by the wearer, and the degree of staining that it is desired to rectify.

V. Methods of Use

In practice, the compositions can be used simply by removing the product from its package, removing a release liner (when included) and applying the adhesive layer to the teeth that it is desired to whiten (or to any body surface if another utility of the whitening agent is to be used). The tooth whitening systems described herein can be provided in a variety of sizes, so that the composition can be applied to the entirety or any portion of a tooth, and to any number of teeth at one time. The substrate, when occlusive, reduces or prevents leakage of the whitening agent, from the composition, while the user wears the composition for the desired amount of time. The composition can be maintained in the desired location for as little time as a few minutes, several hours, all day or overnight, and then removed when the desired degree of whitening has been achieved. If desired, a translucent composition can be provided, and is worn without being obtrusive or noticeable to others.

The composition can be worn for an extended period of time, but will typically be worn for a predetermined period of time of from about 10 minutes to about 24 hours. For tooth whitening application, a preferred time period is from about 10 minutes to about 8 hours (e.g., overnight), with 30 minutes to about 1 hour also being a preferred embodiment.

A user can form the composition around the upper or lower teeth by applying normal manual pressure to the substrate with the tips of the fingers and thumbs, optionally by moistening the composition prior to application. Assuming the surface area of the average adult finger or thumb tip is approximately one square centimeter, the normal pressure generated by the finger and thumb tips is about 100,000 to about 150,000 Pascals (i.e., about 3 lbs. or 1.36 kg) per square centimeter. The pressure is typically applied to the composition by each finger and thumb tip for about one or two seconds. Once the pressure applied to the substrate by the tips of the fingers and thumbs is removed, the composition remains in the shape of, and adherent to, the surface of the teeth and adjoining soft tissue onto which it was formed.

When the user is ready to remove the composition, the composition can be removed simply by peeling it away from the surface of the teeth or other body surface. If desired, the composition can be re-adhered for additional whitening time. Any residue left behind is minimal, and can be removed using conventional tooth cleansing methods.

In one embodiment of the invention, the composition is a solid and is a pressure sensitive adhesive and absorbs water.

The composition can also be applied as a non-solid composition, for example applied as a liquid or gel. For example, the user can extrude the composition from a tube onto a finger for application to the teeth, extrude the composition from a tube directly onto the teeth, apply the composition by means of a brush or other applicator, and so forth. After the evaporation of solvent, the liquid or gel composition dries to form a matrix-type polymer film or gel on the surface of the teeth. In one embodiment of this liquid or gel film-former composition, the hydrogel contains sufficient water or other solvent to provide flowable property. In another embodiment of this composition, the polymer components of the liquid or gel composition are soluble in a water-ethanol mixture both at ambient temperature and at refrigeration temperatures of about 4° C., and are miscible upon solvent evaporation. In yet another embodiment of this liquid or gel film-former composition, the polymeric composition has a Lower Critical Solution Temperature of about 36° C. in an ethanol-water mixture. The resulting film (after solvent evaporation) is preferably insoluble or slowly soluble in saliva at body temperature so as to provide long lasting contact between the hydrogen peroxide and the dental enamel. Finally, the hydrogen peroxide should be stable both in the liquid or gel composition, as well as within polymer film upon drying.

The practice of the present invention will employ, unless otherwise indicated, conventional techniques of polymer chemistry, adhesive manufacture, and hydrogel preparation, which are within the skill of the art. Such techniques are fully explained in the literature.

It is to be understood that while the invention has been described in conjunction with the preferred specific embodiments thereof, the foregoing description, as well as the examples that follow, are intended to illustrate and not limit the scope of the invention. Other aspects, advantages and modifications will be apparent to those skilled in the art to which the invention pertains. All patents, patent applications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in degrees Celsius (° C.), and pressure is at or near atmospheric.

The following abbreviations and tradenames are used in the examples:

Eudragit L100-55 methacrylic acid copolymer, (Rohm America Inc.)
PEG polyethylene glycol 400
PVP Kollidon® 90 polyvinylpyrrolidone (BASF)

EXAMPLES

Example 1

Preparation of a Solid Composition

One embodiment of a composition for tooth whitening was prepared from the following ingredients using a melt extrusion process:

| | |
|---|---|
| Eudragit L100-55 | 9 wt % |
| PVP | 44 wt % |
| PEG | 22 wt % |

| | |
|---|---|
| Hydrogen peroxide | 6 wt % |
| Water, stabilizers, pH modulators | 19 wt % |

The ingredients were melt processed in a Brabender single screw extruder as follows: The Eudragit L100-55 was added to the extruder first, followed by PVP and PEG, at a temperature of 100 to 150° C. The composition was extruded to a thickness of 0.35 mm between two polyethylene terephthalate release liners. Hydrogen peroxide solution was added to the extruded film.

Example 2

In Vitro Release of Hydrogen Peroxide From a Solid Composition

The release of hydrogen peroxide from the tooth whitening compositions of the invention in vitro, in pH 7.0 buffer, was investigated and compared with the peroxide released from a commercial product, Crest Whitestrips™ (a product of the Procter & Gamble Co., Cincinnati, Ohio and referred to as the "Crest product"). The Crest product contains 5.3% hydrogen peroxide in a Carbopol 956 gel on a thin polyethylene film.

The in vitro release of hydrogen peroxide from the compositions containing 3%, 6% or 9% peroxide (formulated as set forth in Example 1) was compared with the release of hydrogen peroxide from the Crest product. The test composition or the Crest product was allowed to release peroxide into solution through filter paper, and the peroxide was measured using standard analytical techniques. For the Crest product, the peroxide levels observed decreased to baseline within about 30 minutes. This data is similar to published data (Pagel, P. A., et al. (2000) Vital Tooth Whitening with a Novel Hydrogen Peroxide Strip System: Design, Kinetics, and Clinical Response. Compendium, Suppl. 29, Vol. 21: S10-S15).

The tooth whitening compositions of the invention released peroxide at a rate proportional to the starting concentration. The compositions of the invention were also found to release peroxide at a higher rate than the Crest product at all times the peroxide content was tested: 5, 30 and 60 minutes. The peroxide release for the composition containing 6% peroxide, which is close to the Crest product, was approximately 7.5, 24 and 10 times greater as the release rate for the Crest product at each time point, respectively. The peroxide release for the composition containing 3% peroxide, was approximately 3, 7 and 5 times greater as the release rate for the Crest product at each time point, respectively.

Example 3

Efficacy of a Solid Composition

The efficacy of the tooth whitening compositions was tested using the following procedure. A subject tested the efficacy of the tooth whitening composition prepared according to the procedure described in Example 1 by applying the composition to the lower set of teeth once a day for 1 hour, for 6 consecutive days. The shade of the subject's teeth was measured using the Professional Tooth Shade Guide before and after treatment of the teeth with the tooth whitening composition. On day 1, the subject's teeth were graded shade 12, and after one hour of treatment with the tooth whitening composition, the teeth were graded shade 10. After one hour of treatment with the tooth whitening composition on day 2, the subject's teeth were graded shade 8. After one hour of treatment on day 3, the subject's teeth were graded shade 5. Similarly, after one hour of treatment on day 4, the subject's teeth were graded shade 4/5. On day 5, after one hour of treatment, the subject's teeth were graded shade 2/3. The lightest shade was achieved after a further one half hour of treatment on day 6, reaching a shade of 2. Thus, the efficacy of the tooth whitening composition was apparent, with measurable results within one hour of treatment.

Example 4

Preparation of a Non-Solid Composition

A composition for tooth whitening was prepared from the following ingredients (Formula A):

| | |
|---|---|
| Deionized water | 35.0 wt % |
| Ethanol | 35.0 wt % |
| Eudragit L 100-55 | 4.00 wt % |
| PEG | 1.00 wt % |
| PVP | 7.00 wt % |
| Carbamide peroxide | 18.0 wt % |
| Sodium citrate | 0.13 wt % |

The composition was mixed in a Cole-Parmer high-torque low-speed lab mixer supplied with Teflon coated impeller (2 inches in diameter) as follows. Deionized water was mixed with ethanol, followed by the addition of PEG. Sodium citrate was then added under vigorous stirring conditions. Eudragit L 100-55 powder was added slowly (with 2-5 min) under vigorous stirring (500-600 rpm). After about 5-10 min it is not necessary to wait until all Eudragit is dissolved), PVP powder was slowly added (within 5 min). The high stirring rate was maintained over 5-10 min. Carbamide peroxide powder was added (within 1-2 min) and the mixture stirred to obtain a homogeneous solution (approximately 30 minutes at 800-900 rpm). The solution was then stored over a period of 2-5 hours to let the air bubbles dissipate.

Example 5

Preparation of a Non-Solid Composition

A composition for tooth whitening was prepared from the following ingredients (Formula B):

| | |
|---|---|
| Deionized water | 35.0 wt % |
| Ethanol | 35.0 wt % |
| Eudragit L 100-55 | 2.50 wt % |
| PEG | 1.92 wt % |
| PVP | 6.00 wt % |
| Carbamide peroxide | 18.0 wt % |
| Sodium Citrate | 0.08 wt % |
| Methocel A4C | 1.50 wt % |

The composition was mixed in a Cole-Parmer high-torque low-speed lab mixer supplied with Teflon coated impeller (2 inches in diameter). Deionized water was mixed with ethanol, followed by the addition of PEG. Sodium citrate was then added under vigorous stirring conditions. Eudragit L 100-55 powder was added slowly (within 5 min) under vigorous stirring (500-600 rpm), followed by the slow (within 5 min) addition of Methocel A4C powder under vigorous stirring (500-600 rpm). After about 10 min, PVP powder was slowly added (within 5 min). The high stirring rate was maintained over 5-10 min. Carbamide peroxide powder was added (within 1-2 min) and the mixture stirred to obtain a homogeneous solution (approximately 30-60 minutes at 500-800 rpm). The solution was then stored over a period of 2-5 hours to let the air bubbles dissipate.

Example 6

In Vitro Dissolution Comparative Study for Non-Solid Composition

The dissolution of the non-solid tooth whitening compositions prepared according to the procedure described in Examples 4 (Formula A) and 5 (Formula B) were compared with the dissolution of a commercial product, Simply White™ clear whitening gel (a product of the Colgate-Palmolive Company, New York, N.Y., and referred to as the "Colgate product"), which contains 18.0 wt % carbamide peroxide. The dissolution process was studied by means of wedge microinterferometry technique.

Formula A was found to form a sharp phase boundary separating the swollen polymer composition from the polymer solution. On the phase boundary a sharp drop of polymer concentration (and hence polymer viscosity) was observed. No such boundary was found to exist in the Colgate product/water interdiffusion zone, whose interference pattern was typical of a completely miscible system with a smooth decrease in polymer concentration (and hence polymer viscosity) in the direction from the composition matrix towards water. Formula B was found to have a heterogeneous (colloidal) nature. A sharp phase boundary was formed between the opaque gel and the translucent aqueous solution. Formula B was also found to have "faster dissolving" fractions and "slower dissolving" fractions. The slower dissolving fractions formed a relatively thin layer encompassing the opaque heterogeneous swollen gel. Contrary to the Colgate product, both Formula A and B upon contact with aqueous media are capable of forming a continuous integrated viscous swollen gel coating separated from a liquid solution by a sharp phase boundary. Formation of the phase boundary for Formula A and B was observed in aqueous media with different pH ranging from 4.6 to 7.5.

Using Formulas A and B, a sharp phase boundary separating swollen polymer from polymer solution is formed. No such boundary exists in the Colgate water inter-diffusion zone whose interference pattern is typical of the completely miscible system with a smooth decrease in polymer concentration (and hence polymer viscosity) in the direction from the Formula A matrix and Formula B matrix towards water.

Effective mass transfer constants of water into Formula A or B and Formula A or B into water are comparable for the Colgate and Formulas A and B. However, contrary to the Colgate product, in the case of the product formation of the sharp phase boundary separating swollen integrated gel from the liquid aqueous solution is observed. The effective diffusion coefficient of the phase boundary is by 1-2 orders lower than those of water into Formula A or B and Formula A or B into water. The swollen gel layer formed by Formulas A and B in the aqueous media is capable of playing a role of protecting coating with sustained dissolution rate. The swollen gel also provides a mechanical support to increase the residence time of Formulas A and B on the teeth surface.

The kinetics of the composition's penetration into water were practically identical for Formulas A and B, whereas the kinetics of the phase boundary displacement were slower for Formula B. The effective mass transfer constants were comparable for the Colgate product and Formulas A and B. However, in the case of Formulas A and B, a sharp phase boundary separating swollen integrated gel from the liquid solution was observed.

In real wear conditions erosion of formulas A and B (and hence their wear time) was mostly dependent on two factors: 1) free interdiffusion processes of the composition and water (saliva) and 2) random mechanical shear stresses imposed upon the coating during wear time (i.e. friction caused by movement of lips). The former factor can be considered as a limiting ideal (undisturbed) process, whereas the later can affect the wear duration in a dramatic and random way, since each coating rapture event changes initial interdiffusion conditions dramatically (i.e. thickness of the coating and composition ingredients). Preliminary wear studies indicated that that Formulas A and B are capable of remaining on teeth for over 10-15 minutes, whereas the Colgate product was found to remain on the teeth for over 2-3 minutes.

Example 7

Comparative In Vitro efficacy for Non-Solid Compositions

The in vitro efficacy of the non-solid tooth whitening composition prepared according to the procedure described in Example 4 (Formula A) was compared with the dissolution of the Colgate product.

A composition of Formula A and the Colgate product were applied on a tea spotted wall of a cup to demonstrate a "first" treatment. After 30 seconds, water was introduced into the cup to cover the coated surface. After 30 minutes, the water was removed and the cup was rinsed with water to remove any remaining gel coating on the wall. The experiment was repeated by applying each composition on the same spot to demonstrate a "second" treatment.

Images of the treated areas were captured by digital camera and the images obtained were converted into 256 pxl grayscale images by using Scion Image software. The images were scaled so that a pxl value of 1 corresponds to an absolute white color and a value of 256 corresponds to an absolute dark color. The intermediate pxl values (from 2 to 255) thus corresponded to intermediate colors, with darkness increasing from 1 to 256. The Scion Image software was also used to measure the color density ($pxl/pxl^2$) of the treated areas. The results, shown below, demonstrate that the composition of Formula A whitens better than the commercially available Colgate product. The higher standard deviation observed for Formula A is explained by less uniformity of the initial tea spot color.

| | Mean Density ($pxl/pxl^2$) (S.D.) | | |
|---|---|---|---|
| | Before treatment | After 1st treatment | After 2nd treatment |
| Colgate product | 194.3 (3.8) | 185.7 (6.2) | 178.0 (6.6) |
| Formula A | 198.3 (5.2) | 178.6 (8.2) | 167.6 (9.0) |

This experiment was repeated using the non-solid tooth whitening composition prepared according to the procedure described in Example 5 (Formula B), except that only a "first" treatment was done.

| | Mean Density (pxl/pxl²) (S.D.) | |
|---|---|---|
| | Before treatment | After 1st treatment |
| Colgate product | 116.9 (6.6) | 89.4 (6.79) |
| Formula B | 117.3 (5.1) | 79.6 (7.3) |

As can be seen from the in vitro data presented above, the whitening efficacy of the composition of Formula A is appreciably superior to the Colgate product, the properties of the composition of Formula B are intermediate between those of the Colgate product and Formula A.

Example 8

In Vitro Release of Hydrogen Peroxide From a Non-Solid Composition

The release of hydrogen peroxide from the non-solid tooth whitening composition of Example 4 (Formula A) was compared with the dissolution of the Colgate product. The Colgate product was cast on a release liner and dried at ambient temperature over one day. The obtained films of the Colgate product, approximately 300-400μ in thickness, were placed into a glass beaker and 200 ml of deionized water added. The composition of Formula A was cast onto a beaker bottom. After 2-3 minutes, 200 ml of deionized water was added. After an appropriate period of time, the solution was accurately separated from the swollen residue and the hydrogen peroxide concentration was determined in accordance with the USP titration method. The amount of hydrogen peroxide released from the Colgate product and Formula A is shown below.

| | Percentage (wt/wt) hydrogen peroxide released Time (minutes) | | | | | | | |
|---|---|---|---|---|---|---|---|---|
| | 1 | 2 | 3 | 5 | 10 | 15 | 20 | 30 |
| Colgate product | — | 38.7 | — | 47.7 | 72.4 | 78.7 | 96.8 | — |
| Formula A | 35.0 | 35.9 | 59.5 | 67.5 | 71.9 | — | 79.2 | 90.0 |

In contrast to the Colgate product, the profile of hydrogen peroxide release from the film formed by Formula A was sustained and characterized by accelerated delivery of the active agent within the first five minutes. Upon 10 minutes of contact with water, Formula A released less hydrogen peroxide than the Colgate product. Upon 20 minutes of contact with water, the Colgate product contained no hydrogen peroxide, whereas Formula A contained 20% of initially loaded hydrogen peroxide. This was evidence of stronger hydrogen peroxide bonding to polymers in Formula A than in the Colgate product. By comparing the release and film dissolution data, it was also concluded that the content of the hydrogen peroxide incorporated into the Formula A film could be categorized as being either loosely bound hydrogen peroxide or toughly bound hydrogen peroxide. This was in contrast to the Colgate product wherein all the hydrogen peroxide was loosely bound.

Example 9

Comparative In Vivo Efficacy of Non-Solid Compositions

The in vivo efficacy of the non-solid tooth whitening composition of Formula A and Formula B were compared with the dissolution of the Colgate product. The whitening efficacy of Formula A and Formula B was compared with that of the Colgate product using the Vita Shade guide value-oriented scale. The study was a randomized, parallel group, double blind pilot study. Eleven subjects with a Vita Shade guide value-oriented scale of A3 or darker on a minimum of four of the six maxillary anterior teeth were recruited to participate in the study.

All 11 subjects were randomly assigned to one of the three treatment groups based upon Vita shade of the maxillary central incisors. The subjects received enough product for 14 days of use and were instructed to used the product twice daily over two weeks. Based upon Vita assessments and subject interviews, it was apparent that Formula A, Formula B and the Colgate product all provided a statistically significant whitening effect since the seventh days of treatment. The best whitening effect was observed for Formula A. Formula B showed a whitening effect that was intermediate between that of Formula A and the Colgate product. Formula A demonstrated an earlier teeth whitening effect compared with the Colgate product.

It is claimed:

1. A tooth whitening system, comprising:
an outer substrate that serves as an external surface of the system following application to a tooth surface;
a tooth contact adhesive layer adhered to the outer substrate, and
a removable release liner positioned on the tooth contact adhesive layer;
wherein the tooth contact adhesive layer comprises a solid composition comprising:
(a) a water-swellable, water-insoluble copolymer of methacrylic acid and ethyl acrylate;
(b) a blend of a poly(N-vinyl lactam) homopolymer and a poly(alkylene glycol) oligomer capable of hydrogen bonding to the poly(N-vinyl lactam); and
(c) a peroxide whitening agent.

2. The tooth whitening system of claim 1, wherein the copolymer has a ratio of free carboxyl groups to ester groups in a range of about 1:1 to 1:2.

3. The tooth whitening system of claim 1, wherein the poly(N-vinyl lactam) is selected from the group consisting of polyvinyl pyrrolidone, polyvinyl caprolactam, and blends thereof.

4. The tooth whitening system of claim 3, wherein the poly(N-vinyl lactam) is polyvinyl pyrrolidone.

5. The tooth whitening system of claim 4, wherein the poly(N-vinyl lactam) has a number average molecular weight in the range of approximately 100,000 to 2,000,000.

6. The tooth whitening system of claim 4, wherein the poly(N-vinyl lactam) has a number average molecular weight in the range of approximately 500,000 to 1,500,000.

7. The tooth whitening system of claim 4, wherein the poly(alkylene glycol) oligomer has a molecular weight in the range of about 45 to 800.

8. The tooth whitening system of claim 7, wherein the poly(alkylene glycol) oligomer is polyethylene glycol.

9. The tooth whitening system of claim 4, wherein the poly(alkylene glycol) oligomer has a molecular weight in the range of about 45 to 600.

10. The tooth whitening system of claim 1, wherein the peroxide is hydrogen peroxide or carbamide peroxide.

11. The tooth whitening system of claim 1, comprising from about 1-20 weight percent of the water-swellable, water insoluble copolymer; from about 20-80 weight percent of the poly(N-vinyl lactam) homopolymer; from about 10-50 weight percent of the poly(alkylene glycol) oligomer; and from about 0.1 to 60 weight percent of the peroxide whitening agent.

12. The tooth whitening system of claim 11, wherein the poly(N-vinyl lactam) homopolymer is polyvinyl pyrrolidone, the poly(alkylene glycol) oligomer is polyethylene glycol, and the whitening agent is a hydrogen peroxide.

13. The tooth whitening system of claim 1, comprising from about 6-12 weight percent of the water-swellable, water insoluble copolymer; from about 40-60 weight percent of the poly(N-vinyl lactam) homopolymer; from about 15-35 weight percent of the poly(alkylene glycol) oligomer; and from about 0.1 to 30 weight percent of the peroxide whitening agent.

14. The tooth whitening system of claim 13, wherein the poly(N-vinyl lactam) homopolymer is polyvinyl pyrrolidone, the poly(alkylene glycol) oligomer is polyethylene glycol, and the whitening agent is a hydrogen peroxide.

15. The tooth whitening system of claim 14, comprising from about 1 to 20 weight percent of the peroxide whitening agent.

16. A method for whitening a tooth, comprising:
    providing a tooth whitening system comprised of (i) an outer substrate that serves as an external surface of the system following application to a tooth surface; (ii) a tooth contact adhesive layer adhered to the outer substrate, and (iii) a removable release liner positioned on the tooth contact adhesive layer;
    wherein the tooth contact adhesive layer comprises a solid composition comprising:
        (a) a water-swellable, water-insoluble copolymer of methacrylic acid and ethyl acrylate;
        (b) a blend of a poly(N-vinyl lactam) homopolymer and a poly(alkylene glycol) oligomer capable of hydrogen bonding to the poly(N-vinyl lactam); and
        (c) a peroxide whitening agent.

17. The method of claim 16, further comprising: removing the release liner and applying the tooth contact adhesive layer to a tooth using manual pressure to the outer substrate.

18. The method of claim 17, wherein after said applying, the tooth contact adhesive layer remains in contact with the tooth for a period of between about 10 minutes to 8 hours.

19. The method of claim 17, wherein after said applying, the tooth contact adhesive layer remains in contact with the tooth for a period of between about 30 minutes to 1 hour.

20. The method of claim 17, further comprising removing the tooth contact adhesive layer from the tooth.

* * * * *